US008530430B2

(12) United States Patent
Nakamura et al.

(10) Patent No.: US 8,530,430 B2
(45) Date of Patent: Sep. 10, 2013

(54) TTK PEPTIDES AND VACCINES INCLUDING THE SAME

(75) Inventors: Yusuke Nakamura, Tokyo (JP); Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: Oncotherapy Science, Inc., Kanagawa (JP)

(*) Notice: Subject to any disclaimer, the term of this patent is extended or adjusted under 35 U.S.C. 154(b) by 0 days.

(21) Appl. No.: 13/320,022

(22) PCT Filed: May 10, 2010

(86) PCT No.: PCT/JP2010/003166
§ 371 (c)(1),
(2), (4) Date: Feb. 3, 2012

(87) PCT Pub. No.: WO2010/131452
PCT Pub. Date: Nov. 18, 2010

(65) Prior Publication Data
US 2012/0135020 A1 May 31, 2012

Related U.S. Application Data

(60) Provisional application No. 61/216,017, filed on May 11, 2009.

(51) Int. Cl.
A61K 38/00 (2006.01)
A61K 38/08 (2006.01)
A61K 39/00 (2006.01)
A61K 38/04 (2006.01)

(52) U.S. Cl.
USPC ....... 514/19.3; 514/21.6; 514/7.5; 424/185.1; 530/328

(58) Field of Classification Search
None
See application file for complete search history.

(56) References Cited

U.S. PATENT DOCUMENTS

| | | | |
|---|---|---|---|
| 6,187,548 B1 * | 2/2001 | Akerstrom et al. | 435/7.2 |
| 7,501,242 B2 * | 3/2009 | Reinhard et al. | 435/6.18 |
| 7,847,060 B2 | 12/2010 | Tahara et al. | |
| 7,998,695 B2 | 8/2011 | Nakamura et al. | |
| 8,053,183 B2 | 11/2011 | Nakamura et al. | |
| 2003/0045491 A1 | 3/2003 | Reinhard et al. | |
| 2006/0024692 A1 | 2/2006 | Nakamura et al. | |
| 2009/0317392 A1 | 12/2009 | Nakamura et al. | |
| 2010/0009920 A1 | 1/2010 | Nakamura et al. | |
| 2010/0040641 A1 | 2/2010 | Tsunoda et al. | |
| 2011/0027302 A1 | 2/2011 | Tahara et al. | |
| 2012/0014996 A1 | 1/2012 | Nakamura et al. | |
| 2012/0021946 A1 | 1/2012 | Nakamura et al. | |

FOREIGN PATENT DOCUMENTS

| | | |
|---|---|---|
| CA | 2438092 A1 | 9/2002 |
| WF | 2007/013665 A2 | 2/2007 |
| WO | 02/068444 A1 | 9/2002 |
| WO | 02/086443 A2 | 10/2002 |
| WO | 2004/031413 A3 | 4/2004 |
| WO | 2004/061423 A2 | 7/2004 |
| WO | 2004/070062 A2 | 8/2004 |
| WO | 2004/094636 A1 | 11/2004 |
| WO | 2005/031002 A2 | 4/2005 |
| WO | 2005/073374 A1 | 8/2005 |
| WO | 2006/059121 A2 | 6/2006 |
| WO | 2006/062811 A2 | 6/2006 |
| WO | 2006/085684 A2 | 8/2006 |
| WO | 2006/090810 A2 | 8/2006 |
| WO | 2007/013671 A2 | 2/2007 |
| WO | 2008/072777 A2 | 6/2008 |
| WO | 2008/102557 A1 | 8/2008 |
| WO | 2009/079768 A1 | 7/2009 |

OTHER PUBLICATIONS

Xu et al., 2012. Vaccine, 30, 2805-2810, 2012.*
Rosenberg et al. 2004. Nat. Med. 10:909-915.*
Frankenberg et al., Eur. J. Cell Biol., 91, 53-58, 2012.*
Robson et al., Curr. Opin. Immunol. 22: 137-144, 2010.*
Schuler et al., Curr. Opin. Immunol. 15: 138-147, 2003.*
Melief et al., Nature Rev. (Cancer), 8, 351-360, 2008.*
Parmiani et al., J. Natl. Ca. Inst., 94, 805-818, 2002.*
Dionne, Sara O., et al., "Her-2/neu altered peptide ligand-induced CTL responses: implications for peptides with increased HLA affinity and T-cell-receptor interaction," Cancer Immunol Immunother, 2004, 53:307-314.
Falk, Kirsten, et al., "Allele-specific motifs revealed by sequencing of self-peptides eluted from MHC molecules," Nature, May 23, 1991, 351:290-296.
Hoffmann, Thomas K., et al., "The Ability of Variant Peptides to Reverse the Nonresponsiveness of T Lymphocytes to the Wild-Type Sequence $p53_{264-272}$ Epitope," J. Immunology, 2002, 168:1338-1347.
Kubo, Ralph T., et al., "Definition of Specific Peptide Motifs for Four Major HLA-A Alleles," J. Immunology, 1994, 152:3913-3924.
Rammensee, Hans-Georg, et al., "MHC ligands and peptide motifs: first listing," Immunogenetics, 1995, 41:178-228.
Zaremba, Sam, et al., "Identification of an Enhancer Agonist Cytotoxic T Lymphocyte Peptide from Human Carcinoembryonic Antigen," Cancer Research, Oct. 15, 1997, 57:4570-4577.

(Continued)

Primary Examiner — Shulamith H Shafer
(74) Attorney, Agent, or Firm — Kilpatrick Townsend & Stockton LLP

(57) ABSTRACT

Peptide vaccines against cancer are described herein. In particular, epitope peptides derived from the TTK gene that elicit CTLs are provided. Antigen-presenting cells and isolated CTLs that target such peptides, as well as methods for inducing the antigen-presenting cell, or CTL are also provided. The present invention further provides pharmaceutical compositions containing as active ingredients peptides derived from TTK or polynucleotides encoding the peptides. Furthermore, the present invention provides methods for the treatment and/or prophylaxis (i.e., prevention) of cancers (tumors), and/or the prevention of postoperative recurrence thereof, as well as methods for inducing CTLs, methods for inducing anti-tumor immunity, using the peptides derived from TTK, polynucleotides encoding the peptides, or antigen-presenting cells presenting the peptides, or the pharmaceutical compositions of the present invention.

13 Claims, 5 Drawing Sheets

(56) References Cited

OTHER PUBLICATIONS

Adams, et al., "Prediction of binding to MHC class I molecules," *J Immunol Methods*, vol. 185(2), pp. 181-190 (Sep. 25, 1995).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Butterfield, et al., "Generation of Human T-cell Responses to an HLA-A2.1-restricted Peptide Epitope Derived from α-Fetoprotein," *Cancer Res.* vol. 59(13), pp. 3134-3142 (Jul. 1, 1999).
Coulie, et al., "Cytolytic T-cell responses of cancer patients vaccinated with a MAGE antigen," *Immunol. Rev.*, vol. 188, pp. 33-42 (Oct. 2002).
Dionne, et al., "Functional characterization of CTL against gp100 altered peptide ligands," *Cancer Immunol. Immunother.*, vol. 52(4), pp. 199-206 (Epub Feb. 18, 2003, Apr. 2003).
Fujie, et al., "A *Mage*-1-Encoded HLA-A24-Binding Synthetic Peptide Induces Specific Anti-Tumor Cytotoxic T Lymphocytes" *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.* vol. 88(20), pp. 88(20), pp. 1442-1455 (Oct. 16, 1996).
Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).
Parker, et al., "Scheme for Ranking Potential HLA-A2 Binding Peptides Based on Independent Binding of Individual Peptide Side Chains," *J Immunol.*, vol. 152(1), pp. 163-175 (Jan. 1, 1994).
Rosenberg, et al., "Cancer Immunotherapy: moving beyond current vaccines," *Nat Med.*, vol. 10(9),.pp. 909-915 (Sep 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).
Abrieu, et al., "Mps1 Is a Kinetochore-Associated Kinase Essential for the Vertebrate Mitotic Checkpoint," *Cell*, vol. 106(1), pp. 83-93 (Jul. 13, 2001).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).

Cahill, et al., "Characterization of *MAD2B* and Other Mitotic Spindle Checkpoint Genes," *Genomics*, vol. 58(2), pp. 181-187 (Jun. 1, 1999).
Chen, et al., "Overexpression of Oncoprotein 18 Correlates with Poor Differentiation in Lung Adenocarcinomas," *Mol Cell Proteomics*, vol. 2(2), pp. 107-116 (Epub Feb. 12, 2003).
Haruki, et al., "Molecular analysis of the mitotic checkpoint genes *BUB1, BUBR1, and BUB3* in human lung cancers," *Cancer Lett.* vol. 162(2), pp. 201-205 (Jan. 26, 2001).
Hoshikawa, et al., "Hypoxia induces different genes in the lungs of rats compared with mice," *Physiol Genomics*, vol. 12(3), pp. 209-219 (Feb. 6, 2003).
Iinuma, et al., "Novel Peptide Vaccine Therapy Combined with Chemoradiation for Advanced or Recurrent Esophageal Cancer," *Biotherapy*, 22 suppl. I:129, W8-3 (Nov. 2008).
Kikuchi, et al., "Expression profiles of metastatic brain tumor from lung adenocarcinomas on cDNA microarray," *Int J Oncol.*, vol. 28(4), pp. 799-805 (Apr. 2006).
Kono, et al. "Vaccination with multiple peptides derived from novel cancer-testis antigens can induce specific T-cell responses and clinical responses in advanced esophageal cancer," *Cancer Sci.*, vol. 100(8), pp. 1502-1509 (Epub May 14, 2009, Aug. 2009).
Landi, et al., "Gene Expression Signature of Cigarette Smoking and Its Role in Lung Adenocarcinoma Development and Survival," *Plos One*, vol. 3(2):e1651, pp. 1-8 (Feb. 20, 2008).
Mills, et al., "Expression of TTK, a Novel Human Protein Kinase, Is Associated with Cell Proliferation," *J. Biol Chem.*, vol. 267(22), pp. 16000-16006 (Aug. 5, 1992).
Mimori, et al., "Mutation of hBUB1, human mitotic checkpoint gene in multiple carcinomas," *Oncol Rep.*, vol. 8(1), pp. 39-42 (Jan. 2001-Feb. 2001).
Mizukami, et al., "Detection of novel cancer-testis antigen-specific T-cell responses in TIL, regional lymph nodes, and PBL in patients with esophageal squamous cell carcinoma," *Cancer Sci.*, vol. 99(7), pp. 1448-1454 (Epub Apr. 30, 2008, Jul. 2008).
Schmandt, et al., "IL-2-Induced Expression of TTK, a Serine, Threonine, Tyrosine Kinase, Correlates with Cell Cycle Progression," *J Immunol.*, vol. 152(1), pp. 96-105 (Jan. 1, 1994).
Stucke, et al., "Human Mps1 kinase is required for the spindle assembly checkpoint but not for centrosome duplication," *Embo J.*, vol. 21(7), pp. 1723-1732 (Apr. 2, 2002).
Suda, et al., "Identification of human leukocyte antigen-A24-restricted epitope peptides derived from gene products upregulated in lung and esophageal cancers as novel targets for immunotherapy," *Cancer Science*, vol. 98(11), pp. 1803-1808 (Nov. 10, 2007).
Tahara, Slides for the Symposium of the Japanese Cancer Association, 8 pages (Feb. 7, 2006).
Weiss, et al., "The *Saccharomyces cerevisiae* Spindle Pole Body Duplication Gene MPS1 Is Part of a Mitotic Checkpoint," *J Cell Biol.*, vol. 132(1-2), pp. 111-123 (Jan. 1996).
Winey, et al., "*MPS1* and *MPS2*: Novel Yeast Genes Defining Distinct Steps of Spindle Pole Body Duplication," *J Cell Biol.* vol. 114(4), pp. 745-754 (Aug. 1991).
Genbank Accession No. NM_003318, dated Sep. 25, 2002, 3 pages.
U.S. Appl. No. 13/464,831, filed May 4, 2012, 162 pages.
U.S. Appl. No. 13/536,327, filed Jun. 28, 2012, 204 pages.
International Search Report for PCT/JP2010/003166, mailed Jun. 15, 2010, 6 pages.
U.S. Appl. No. 13/744,354, filed Jan. 17, 2013, 124 pages.

\* cited by examiner

Fig. 2a-d
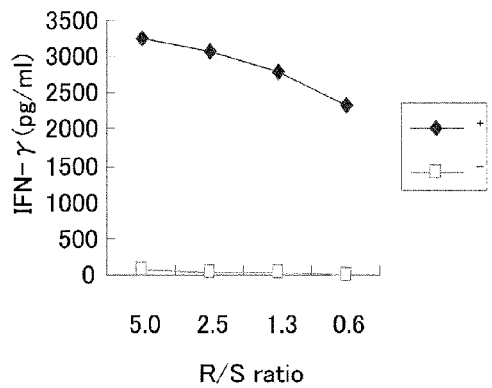
a  TTK-A02-9-462 #1
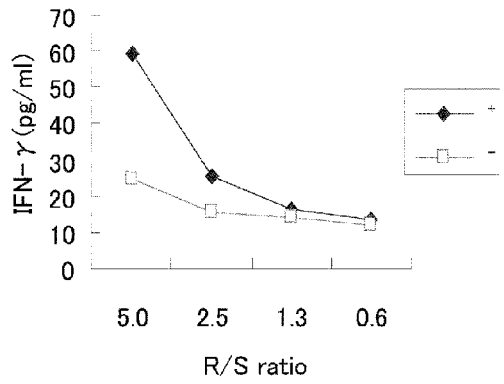
b  TTK-A02-9-630 #7
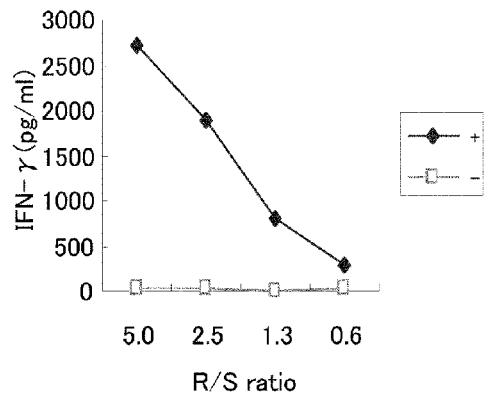
c  TTK-A02-9-593 #5
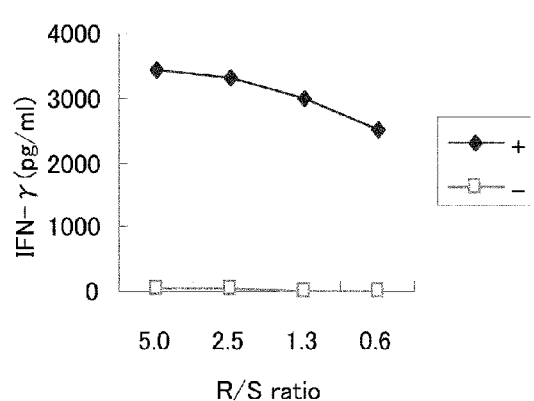
d  TTK-A02-9-719 #5

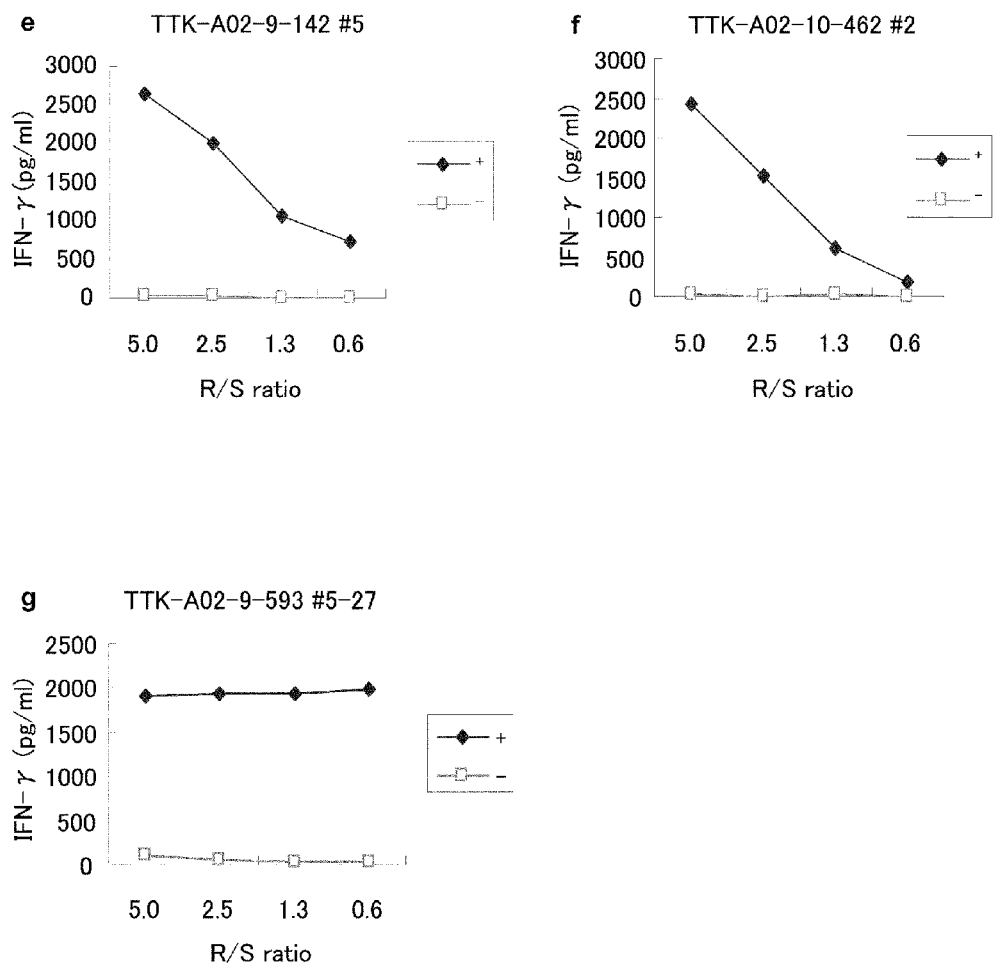

Fig. 4
Reference Data: The data of Endo Assays in Figs. of WO2008/102557.
WO08102557_Fig.8b
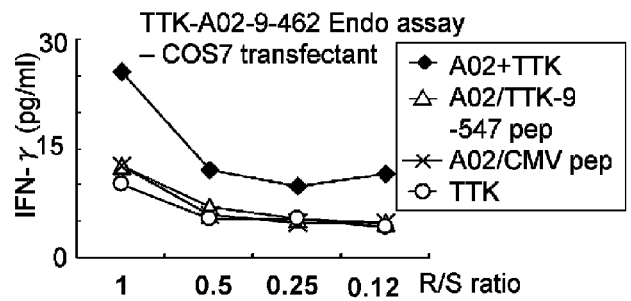
WO08102557_Fig.8c
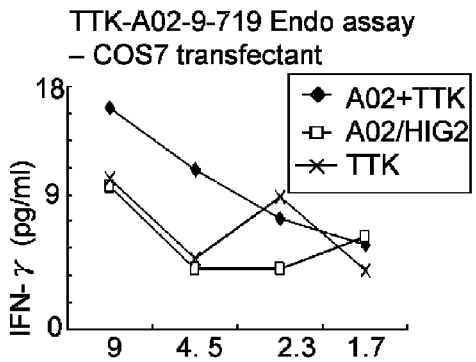
WO08102557_Fig.8d
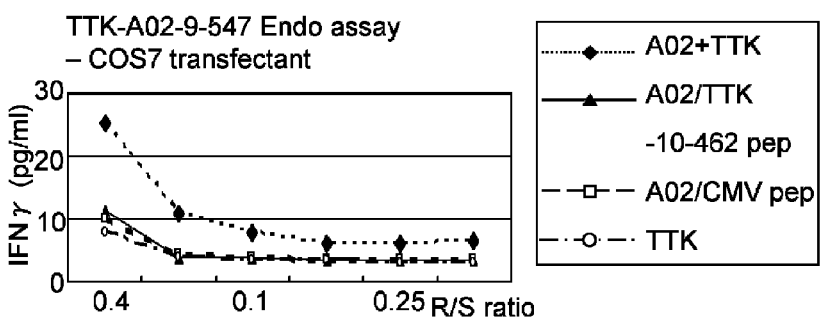
WO08102557_Fig.8e
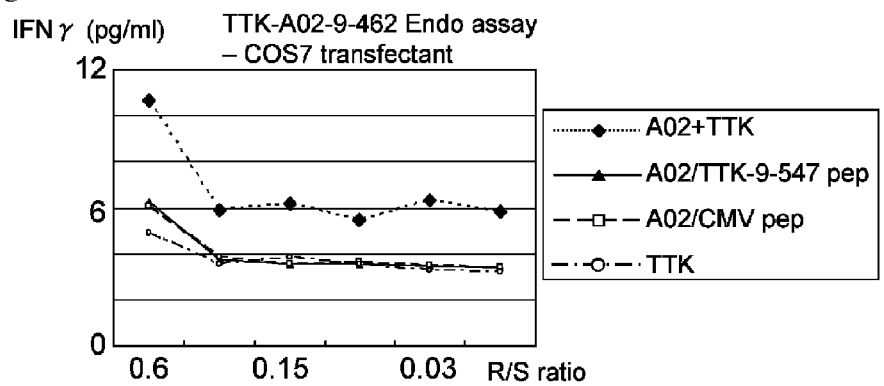

ional Phase of PCT/

SEQUENCE LISTING

```
<160> NUMBER OF SEQ ID NOS: 44

<210> SEQ ID NO 1
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 1

Tyr Met Ser Cys Phe Arg Thr Pro Val
```

-continued

```
<210> SEQ ID NO 2
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 2

Asn Met Leu Glu Ala Val His Thr Ile
1               5

<210> SEQ ID NO 3
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 3

Ile Thr Asp Gln Tyr Ile Tyr Met Val
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 4

Gln Met Gln Pro Asp Thr Thr Ser Val
1               5

<210> SEQ ID NO 5
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 5

Lys Gln Ile Tyr Ala Ile Lys Tyr Val
1               5

<210> SEQ ID NO 6
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 6

Ser Leu Gly Cys Ile Leu Tyr Tyr Met
1               5

<210> SEQ ID NO 7
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 7

Tyr Val Leu Gly Gln Leu Val Gly Leu
1               5
```

```
<210> SEQ ID NO 8
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 8

Tyr Val Gln Ile Gln Thr His Pro Val
1               5

<210> SEQ ID NO 9
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 9

Leu Ile Val Asp Gly Met Leu Lys Leu
1               5

<210> SEQ ID NO 10
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 10

Thr Ile Asp Ser Ile Met Asn Lys Val
1               5

<210> SEQ ID NO 11
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 11

Met Leu Lys Leu Ile Asp Phe Gly Ile
1               5

<210> SEQ ID NO 12
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 12

Ser Leu Leu Ala Lys Leu Glu Glu Thr
1               5

<210> SEQ ID NO 13
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 13

Ile Leu Ala Thr Pro Leu Gln Asn Leu
1               5

<210> SEQ ID NO 14
```

```
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 14

Leu Ile Ile Thr Asp Ser Ile Thr Leu
1               5

<210> SEQ ID NO 15
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 15

Phe Ala Phe Val His Ile Ser Phe Ala
1               5

<210> SEQ ID NO 16
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 16

Ala Ile Ile Asp Pro Asn His Glu Ile
1               5

<210> SEQ ID NO 17
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 17

Lys Leu Ile Gly Arg Tyr Ser Gln Ala
1               5

<210> SEQ ID NO 18
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 18

Leu Leu Ala His Pro Tyr Val Gln Ile
1               5

<210> SEQ ID NO 19
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 19

His Ile Ser Phe Ala Gln Phe Glu Leu
1               5

<210> SEQ ID NO 20
<211> LENGTH: 9
<212> TYPE: PRT
```

-continued

```
<213> ORGANISM: Artificial
<220> FEATURE:
<223> OTHER INFORMATION: an artificially synthesized peptide sequence

<400> SEQUENCE: 20

Thr Leu Asp Ser Tyr Arg Asn Glu Ile
1               5

<210> SEQ ID NO 21
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 21

Tyr Met Val Met Glu Cys Gly Asn Ile
1               5

<210> SEQ ID NO 22
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 22

Tyr Met Ser Cys Phe Arg Thr Pro Val Val
1               5                   10

<210> SEQ ID NO 23
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 23

Phe Leu Ile Val Asp Gly Met Leu Lys Leu
1               5                   10

<210> SEQ ID NO 24
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 24

Gly Met Leu Lys Leu Ile Asp Phe Gly Ile
1               5                   10

<210> SEQ ID NO 25
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 25

Phe Leu Tyr Gly Glu Asn Met Pro Pro Gln
1               5                   10

<210> SEQ ID NO 26
<211> LENGTH: 10
<212> TYPE: PRT
<213> ORGANISM: Artificial
<220> FEATURE:
```

<223> OTHER INFORMATION: an artificially synthesized peptide sequence

<400> SEQUENCE: 26

Lys Leu Ile Gly Arg Tyr Ser Gln Ala Ile
1               5                   10

<210> SEQ ID NO 27
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 27

Thr Thr Phe Glu Gln Pro Val Phe Ser Val
1               5                   10

<210> SEQ ID NO 28
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 28

Gln Met Gln Pro Asp Thr Thr Ser Val Val
1               5                   10

<210> SEQ ID NO 29
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 29

Met Val Met Glu Cys Gly Asn Ile Asp Leu
1               5                   10

<210> SEQ ID NO 30
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 30

Asn Leu Ser Ala Ser Thr Val Leu Thr Ala
1               5                   10

<210> SEQ ID NO 31
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 31

Leu Thr Ile Asp Ser Ile Met Asn Lys Val
1               5                   10

<210> SEQ ID NO 32
<211> LENGTH: 10
<212> TYPE: PRT
<213> ORGANISM: Artificial
<220> FEATURE:
<223> OTHER INFORMATION: an artificially synthesized peptide sequence

```
<400> SEQUENCE: 32

Lys Ile Ile Arg Leu Tyr Asp Tyr Glu Ile
1               5                   10

<210> SEQ ID NO 33
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 33

Met Met Ala Asn Asn Pro Glu Asp Trp Leu
1               5                   10

<210> SEQ ID NO 34
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 34

Val Leu Asn Glu Lys Lys Gln Ile Tyr Ala
1               5                   10

<210> SEQ ID NO 35
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 35

Lys Leu Ile Asp Phe Gly Ile Ala Asn Gln
1               5                   10

<210> SEQ ID NO 36
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 36

Leu Leu Leu Lys Leu Glu Lys Asn Ser Val
1               5                   10

<210> SEQ ID NO 37
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 37

Gln Met Ala Lys Gly Thr Thr Glu Glu Met
1               5                   10

<210> SEQ ID NO 38
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 38
```

```
Gln Ile Tyr Ala Ile Lys Tyr Val Asn Leu
1               5                   10

<210> SEQ ID NO 39
<211> LENGTH: 2984
<212> TYPE: DNA
<213> ORGANISM: Homo sapiens

<400> SEQUENCE: 39
ggaaattcaa acgtgtttgc ggaaaggagt ttgggttcca tcttttcatt tccccagcgc      60
agctttctgt agaaatggaa tccgaggatt taagtggcag agaattgaca attgattcca     120
taatgaacaa agtgagagac attaaaaata gtttaaaaa tgaagacctt actgatgaac      180
taagcttgaa taaaatttct gctgatacta cagataactc gggaactgtt aaccaaatta     240
tgatgatggc aaacaaccca gaggactggt tgagtttgtt gctcaaacta gagaaaaaca     300
gtgttccgct aagtgatgct ctttaaata aattgattgg tcgttacagt caagcaattg      360
aagcgcttcc cccagataaa tatggccaaa atgagagttt gctagaatt caagtgagat      420 ttgctgaatt aaaagctatt caagagccag atgatgcacg tgactacttt caaatggcca     480
gagcaaactg caagaaattt gcttttgttc atatatcttt tgcacaattt gaactgtcac     540
aaggtaatgt caaaaaaagt aaacaacttc ttcaaaaagc tgtagaacgt ggagcagtac     600
cactagaaat gctggaaatt gccctgcgga atttaaacct ccaaaaaaag cagctgcttt     660
cagaggagga aagaagaat ttatcagcat ctacggtatt aactgcccaa gaatcatttt      720
ccggttcact tggcatta cagaatagga caacagttg tgattccaga ggacagacta       780
ctaaagccag gttttatat ggagagaaca tgccaccaca agatgcagaa ataggttacc      840
ggaattcatt gagacaaact aacaaaacta acagtcatg cccatttgga agagtcccag      900
ttaaccttct aaatagccca gattgtgatg tgaagacaga tgattcagtt gtaccttgtt     960
ttatgaaaag acaaacctct agatcagaat gccgagattt ggttgtgcct ggatctaaac    1020
caagtggaaa tgattcctgt gaattaagaa atttaaagtc tgttcaaaat agtcatttca    1080
aggaacctct ggtgtcagat gaaaagagtt ctgaacttat tattactgat tcaataaccc    1140
tgaagaataa aacggaatca agtcttctag ctaaattaga agaaactaaa gagtatcaag    1200
aaccagaggt tccagagagt aaccagaaac agtggcaatc taagaaaag tcagagtgta     1260 ttaaccagaa tcctgctgca tcttcaaatc actggcagat tccggagtta gcccgaaaag    1320
ttaatacaga gcagaaacat accacttttg agcaacctgt cttttcagtt tcaaaacagt    1380
caccaccaat atcaacatct aaatgggttg acccaaaatc tatttgtaag acaccaagca    1440
gcaatacctt ggatgattac atgagctgtt ttagaactcc agttgtaaag aatgactttc    1500
cacctgcttg tcagttgtca cacccttatg gccaacctgc ctgtttccag cagcaacagc    1560
atcaaatact tgccactcca cttcaaaatt tacaggtttt agcatcttct tcagcaaatg    1620
aatgcatttc ggttaaagga agaatttatt ccatttttaaa gcagatagga agtggaggtt    1680
caagcaaggt atttcaggtg ttaaatgaaa agaaacagat atatgctata aaatatgtga    1740
acttagaaga agcagataac caaactcttg atagttaccg gaacgaaata gcttatttga    1800
ataaactaca caacacagt gataagatca tccgacttta tgattatgaa atcacggacc     1860
agtacatcta catggtaatg gagtgtggaa atattgatct aatagttgg cttaaaaga      1920 aaaaatccat tgatccatgg gaacgcaaga gttactggaa aaatatgtta gaggcagttc    1980
acacaatcca tcaacatggc attgttcaca gtgatcttaa accagctaac tttctgatag    2040
ttgatggaat gctaaagcta attgattttg ggattgcaaa ccaaatgcaa ccagatacaa    2100
```

```
caagtgttgt taaagattct caggttggca cagttaatta tatgccacca gaagcaatca    2160
aagatatgtc ttcctccaga gagaatggga aatctaagtc aaagataagc cccaaaagtg    2220
atgtttggtc cttaggatgt attttgtact atatgactta cgggaaaaca ccatttcagc    2280
agataattaa tcagatttct aaattacatg ccataattga tcctaatcat gaaattgaat    2340
ttcccgatat tccagagaaa gatcttcaag atgtgttaaa gtgttgttta aaaagggacc    2400
caaaacagag gatatccatt cctgagctcc tggctcatcc ctatgttcaa attcaaactc    2460
atccagttaa ccaaatggcc aagggaacca ctgaagaaat gaaatatgtt ctgggccaac    2520
ttgttggtct gaattctcct aactccattt tgaaagctgc taaaactttta tatgaacact    2580 atagtggtgg tgaaagtcat aattcttcat cctccaagac ttttgaaaaa aaagggggaa    2640
aaaaatgatt tgcagttatt cgtaatgtca aataccacct ataaaatata ttggactgtt    2700
atactcttga tcccctgtgg aaatctacat ttgaagacaa catcactctg aagtgttatc    2760
agcaaaaaaa attcagtaga ttatctttaa aagaaaactg taaaaatagc aaccacttat    2820
ggtactgtat atattgtaga cttgttttct ctgttttatg ctcttgtgta atctacttga    2880
catcatttta ctcttggaat agtgggtgga tagcaagtat attctaaaaa actttgtaaa    2940
taaagttttg tggctaaaat gacactaaaa aaaaaaaaaa aaaa                    2984
```

<210> SEQ ID NO 40
<211> LENGTH: 857
<212> TYPE: PRT
<213> ORGANISM: Homo sapiens

<400> SEQUENCE: 40

```
Met Glu Ser Glu Asp Leu Ser Gly Arg Glu Leu Thr Ile Asp Ser Ile
1               5                   10                  15

Met Asn Lys Val Arg Asp Ile Lys Asn Lys Phe Lys Asn Glu Asp Leu
            20                  25                  30

Thr Asp Glu Leu Ser Leu Asn Lys Ile Ser Ala Asp Thr Thr Asp Asn
        35                  40                  45

Ser Gly Thr Val Asn Gln Ile Met Met Met Ala Asn Asn Pro Glu Asp
    50                  55                  60

Trp Leu Ser Leu Leu Leu Lys Leu Glu Lys Asn Ser Val Pro Leu Ser
65                  70                  75                  80

Asp Ala Leu Leu Asn Lys Leu Ile Gly Arg Tyr Ser Gln Ala Ile Glu
                85                  90                  95

Ala Leu Pro Pro Asp Lys Tyr Gly Gln Asn Glu Ser Phe Ala Arg Ile
            100                 105                 110

Gln Val Arg Phe Ala Glu Leu Lys Ala Ile Gln Glu Pro Asp Asp Ala
        115                 120                 125

Arg Asp Tyr Phe Gln Met Ala Arg Ala Asn Cys Lys Lys Phe Ala Phe
    130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Lys Lys Asn Leu Ser Ala Ser Thr Val
        195                 200                 205

Leu Thr Ala Gln Glu Ser Phe Ser Gly Ser Leu Gly His Leu Gln Asn
    210                 215                 220
```

```
Arg Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
            245                 250                 255

Asn Ser Leu Arg Gln Thr Asn Lys Thr Lys Gln Ser Cys Pro Phe Gly
                260                 265                 270

Arg Val Pro Val Asn Leu Leu Asn Ser Pro Asp Cys Asp Val Lys Thr
            275                 280                 285

Asp Asp Ser Val Val Pro Cys Phe Met Lys Gln Thr Ser Arg Ser
290                 295                 300

Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
                325                 330                 335

Glu Pro Leu Val Ser Asp Glu Lys Ser Ser Glu Leu Ile Ile Thr Asp
            340                 345                 350

Ser Ile Thr Leu Lys Asn Lys Thr Glu Ser Ser Leu Leu Ala Lys Leu
                355                 360                 365

Glu Glu Thr Lys Glu Tyr Gln Glu Pro Glu Val Pro Glu Ser Asn Gln
            370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                405                 410                 415

Asn Thr Glu Gln Lys His Thr Thr Phe Glu Gln Pro Val Phe Ser Val
            420                 425                 430

Ser Lys Gln Ser Pro Pro Ile Ser Thr Ser Lys Trp Phe Asp Pro Lys
                435                 440                 445

Ser Ile Cys Lys Thr Pro Ser Ser Asn Thr Leu Asp Asp Tyr Met Ser
450                 455                 460

Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
                500                 505                 510

Ser Ala Asn Glu Cys Ile Ser Val Lys Gly Arg Ile Tyr Ser Ile Leu
                515                 520                 525

Lys Gln Ile Gly Ser Gly Gly Ser Ser Lys Val Phe Gln Val Leu Asn
            530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
            580                 585                 590

Ile Thr Asp Gln Tyr Ile Tyr Met Val Met Glu Cys Gly Asn Ile Asp
            595                 600                 605

Leu Asn Ser Trp Leu Lys Lys Lys Ser Ile Asp Pro Trp Glu Arg
            610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
```

```
                        645                 650                 655
Asp Gly Met Leu Lys Leu Ile Asp Phe Gly Ile Ala Asn Gln Met Gln
            660                 665                 670

Pro Asp Thr Thr Ser Val Val Lys Asp Ser Gln Val Gly Thr Val Asn
        675                 680                 685

Tyr Met Pro Pro Glu Ala Ile Lys Asp Met Ser Ser Ser Arg Glu Asn
    690                 695                 700

Gly Lys Ser Lys Ser Lys Ile Ser Pro Lys Ser Asp Val Trp Ser Leu
705                 710                 715                 720

Gly Cys Ile Leu Tyr Tyr Met Thr Tyr Gly Lys Thr Pro Phe Gln Gln
                725                 730                 735

Ile Ile Asn Gln Ile Ser Lys Leu His Ala Ile Ile Asp Pro Asn His
            740                 745                 750

Glu Ile Glu Phe Pro Asp Ile Pro Glu Lys Asp Leu Gln Asp Val Leu
        755                 760                 765

Lys Cys Cys Leu Lys Arg Asp Pro Lys Gln Arg Ile Ser Ile Pro Glu
    770                 775                 780

Leu Leu Ala His Pro Tyr Val Gln Ile Gln Thr His Pro Val Asn Gln
785                 790                 795                 800

Met Ala Lys Gly Thr Thr Glu Glu Met Lys Tyr Val Leu Gly Gln Leu
                805                 810                 815

Val Gly Leu Asn Ser Pro Asn Ser Ile Leu Lys Ala Ala Lys Thr Leu
            820                 825                 830

Tyr Glu His Tyr Ser Gly Gly Glu Ser His Asn Ser Ser Ser Ser Lys
        835                 840                 845

Thr Phe Glu Lys Lys Arg Gly Lys Lys
    850                 855

<210> SEQ ID NO 41
<211> LENGTH: 22
<212> TYPE: DNA
<213> ORGANISM: Artificial Sequence
<220> FEATURE:
<223> OTHER INFORMATION: an artificially synthesized nucleotide sequence

<400> SEQUENCE: 41
gtctaccagg cattcgcttc at                                          22

<210> SEQ ID NO 42
<211> LENGTH: 24
<212> TYPE: DNA
<213> ORGANISM: Artificial Sequence
<220> FEATURE:
<223> OTHER INFORMATION: an artificially synthesized nucleotide sequence

<400> SEQUENCE: 42
tcagctggac cacagccgca gcgt                                        24

<210> SEQ ID NO 43
<211> LENGTH: 21
<212> TYPE: DNA
<213> ORGANISM: Artificial Sequence
<220> FEATURE:
<223> OTHER INFORMATION: an artificially synthesized nucleotide sequence

<400> SEQUENCE: 43
tcagaaatcc tttctcttga c                                           21

<210> SEQ ID NO 44
<211> LENGTH: 24
```

```
<212> TYPE: DNA
<213> ORGANISM: Artificial Sequence
<220> FEATURE:
<223> OTHER INFORMATION: an artificially synthesized nucleotide sequence

<400> SEQUENCE: 44
ctagcctctg gaatcctttc tctt                                          24
```

TTK PEPTIDES AND VACCINES INCLUDING THE SAME

PRIORITY

The present application is a U.S. National Phase of PCT/JP2010/003166, filed May 10, 2010, which claims the benefit of U.S. Provisional Applications No. 61/216,017, filed on May 11, 2009, the entire contents of which are incorporated by reference herein in their entirety.

REFERENCE TO A SEQUENCE LISTING

This application includes a Sequence Listing as a text file named "SEQTXT_87331-823934 019810US.txt" created Nov. 10, 2011 and containing 20,725 bytes. The material contained in this text file is incorporated by reference in its entirety for all purposes.

The present invention relates to the field of biological science, more specifically to the field of cancer therapy. In particular, the present invention relates to novel peptides that are extremely effective as cancer vaccines and drugs for treating and preventing tumors.

TECHNICAL FIELD

Background Art

It has been demonstrated that CD8 positive CTLs recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered primarily through immunological approaches (NPL 1/Boon T, Int J Cancer 1993 May 8, 54(2): 177-80; NPL 2/Boon T & van der Bruggen P, J Exp Med 1996 Mar. 1, 183(3): 725-9). Some of these TAAs are in currently undergoing clinical development as immunotherapeutic targets.

Identification of new TAAs capable of inducing potent and specific anti-tumor immune responses warrants further development and clinical investigation of peptide vaccination strategies for various types of cancer is ongoing (NPL 3/Harris C C, J Natl Cancer Inst 1996 Oct. 16, 88(20): 1442-55; NPL 4/Butterfield L H et al., Cancer Res 1999 Jul. 1, 59(13): 3134-42; NPL 5/Vissers J L et al., Cancer Res 1999 Nov. 1, 59(21): 5554-9; NPL 6/van der Burg S H et al., J Immunol 1996 May 1, 156(9): 3308-14; NPL 7/Tanaka F et al., Cancer Res 1997 Oct. 15, 57(20): 4465-8; NPL 8/Fujie T et al., Int J Cancer 1999 Jan. 18, 80(2): 169-72; NPL 9/Kikuchi M et al., Int J Cancer 1999 May 5, 81(3): 459-66; NPL 10/Oiso M et al., Int J Cancer 1999 May 5, 81(3): 387-94). Unfortunately, many of the current cancer vaccine trials have shown only a low objective response rate (NPL 11/Belli F et al., J Clin Oncol 2002 Oct. 15, 20(20): 4169-80; NPL 12/Coulie P G et al., Immunol Rev 2002 October, 188: 33-42; NPL 13/Rosenberg S A et al., Nat Med 2004 September, 10(9): 909-15). Accordingly, there remains a need for new TAAs as immunotherapeutic targets.

To that end, a number of up-regulated genes have been identified in small cell lung cancers (SCLCs) (PTL1/WO2007/013665) and esophageal cancers (PTL2/WO2007/013671) through analyses of gene-expression profiles using genome-wide cDNA microarrays. These genes have been amply investigated with the hopes of identifying good candidates as immunotherapeutic targets from among them. In order to target cancer cells specifically in immunotherapy, preferred TAAs should be expressed primarily by cancer cells, with limited or no expression by normal healthy tissues. Preferred TAAs as immunotherapy targets are those that are indispensable for proliferation and survival of cancer cells. Such TAAs may minimize the well-described risk of immune escape of cancer cells attributable to deletion, mutation, or down-regulation of TAAs as a consequence of therapeutically driven immune selection.

Using gene expression profiling with a genome-wide cDNA microarray containing 23,040 genes, TTK Protein kinase (TTK) was identified as one of the genes up-regulated in lung cancer (NPL3/Kikuchi at al., Int J Oncol. 2006 April; 28(4):799-805). Expression of TTK is specifically up-regulated in tumor cells in more than 80% of the patients with lung cancer and esophageal cancer. At the same time, TTK is not expressed in any other normal vital organ, except the testis. Taken together, these facts suggest TTK may be applicable as a target of cancer immunotherapy for patient with TTK up-regulated tumors. Peptides derived from TTK that have specific CTL inducibility against target cells exogenously expressing TTK and HLA-A*0201 have previously been disclosed (See WO2008/102557 (PTL3), the results of which are duplicated herein as FIG. 4).

CITATION LIST

Patent Literature

[PTL 1] WO2007/013665
[PTL 2] WO2007/013671
[PTL 3] WO2008/102557

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL3] Kikuchi at al., Int J Oncol. 2006 April; 28(4):799-805

SUMMARY OF INVENTION

The present invention is based, at least in part, on the discovery of novel peptides that may serve as targets of immunotherapy. Because TAAs are sometimes perceived by the immune system as "self" and therefore often have no innate immunogenicity, the discovery of appropriate targets is of extreme importance. As noted above, TTK (a typical amino acid sequence and gene sequence are shown in SEQ ID NO: 40 and SEQ ID NO: 39, respectively, but are not limited to, and a typical gene sequence is also available from, for example, GenBank Accession No. NM_003318) has been identified as up-regulated in cancers, including, but not limited to, lung cancer, bladder cancer, breast cancer, cervical cancer, cholangiocellular carcinoma, Chronic myelogenous leukemia (CML), colorectal cancer, endometriosis, esophageal cancer, gastric cancer, diffused type gastric cancer, liver cancer, non-small cell lung cancer (NSCLC), lymphoma, osteosarcoma, ovarian cancer, pancreatic cancer, prostate cancer, renal carcinoma, small cell lung cancer (SCLC), soft tissue tumor and testicular tumor. Thus, the present invention focuses on TTK as a candidate for the target of cancer/tumor immunotherapy.

The present invention further relates to the identification of specific epitope peptides of the gene products of TTK that possess the ability to induce CTLs specific to TTK. As discussed in detail below, peripheral blood mononuclear cells (PBMCs) obtained from a healthy donor were stimulated using HLA-A*0201 binding candidate peptides derived from TTK. CTL lines were then established with specific cytotoxicity against the HLA-A2 positive target cells pulsed with each of candidate peptides. Among those CTL lines, CTL lines induced with a peptide having an amino acid sequence of SEQ ID NO: 3 showed significantly potent specific cytotoxicity against cells expressing HLA-A*0201 and TTK. These results demonstrate that these peptides (especially a peptide having an amino acid sequence of SEQ ID NO: 3) are HLA-A2 restricted epitope peptides that may induce potent and specific immune responses against cells expressing TTK. Further, the results indicate that TTK is strongly immunogenic and the epitopes thereof are effective targets for cancer/tumor immunotherapy.

Accordingly, it is an object of the present invention to provide isolated peptides that bind to HLA antigen, particularly those that include an amino acid sequence of TTK (e.g., SEQ ID NO: 40) or an immunologically active fragment thereof. These peptides are expected to have CTL inducibility and, thus, can be used to induce CTL ex vivo or to be administered to a subject for inducing immune responses against cancers such as lung cancer, bladder cancer, breast cancer, cervical cancer, cholangincellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Preferred peptides are peptides having an amino acid sequence of SEQ ID NO: 3.

The peptides of the present invention encompass those wherein one, two or more amino acids are substituted, deleted and/or added, so long as the resulting modified peptides retain the original CTL inducibility.

The present invention also provides isolated polynucleotides encoding any peptides of the present invention. These polynucleotides can be used for inducing or preparing APCs with CTL inducibility or can be administered to a subject for inducing immune responses against cancers much like the present peptides.

When administered to a subject, the present peptides are preferably presented on the surface of APCs so as to induce CTLs targeting the respective peptides. Therefore, one object of the present invention is to provide agents or compositions that induce CTLs, such agents or compositions including one or more peptides of the present invention or polynucleotides encoding such peptides. The present invention further contemplates pharmaceutical agents or compositions including one or more peptides of the present invention or polynucleotides encoding such peptides, such agents or compositions formulated for the treatment and/or prophylaxis of cancers, as well as the prevention of postoperative recurrence thereof, such cancers including, but not limited, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. The present pharmaceutical agents or compositions can include APCs or exosomes that present any of the present peptides instead of/in addition to the present peptides or polynucleotides as active ingredients.

The peptides and polynucleotides of the present invention can induce APCs that present on their surface a complex of an HLA antigen and the present peptide, for example, by contacting APCs derived from a subject with the peptide or introducing a polynucleotide encoding a peptide of the present invention into APCs. Such APCs have high CTL inducibility against target peptides and thus find use in cancer immunotherapy. Accordingly, the present invention contemplates both methods for inducing APCs with CTL inducibility and APCs obtained by such methods.

The present invention also provides methods for inducing CTL, methods that include the step of co-culturing CD8 positive cells with APCs or exosomes presenting one or more peptides of the present invention on its surface or the step of introducing a gene that includes a polynucleotide encoding a T cell receptor (TCR) subunit polypeptide capable of bind to the present peptide. CTLs obtained by such methods find use in the treatment and prevention of cancers, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Therefore, the present invention encompasses the CTLs obtained by the present methods. It is another object of the present invention to provide methods for inducing an immune response against cancers in a subject in need thereof, such methods including the step of administering to the subject a agent or composition that includes a TTK polypeptide or an immunologically active fragment thereof, polynucleotides encoding a TTK polypeptide, and exosomes or APCs presenting a TTK polypeptide.

The applicability of the present invention extends to any of a number of diseases relating to or arising from TTK overexpression, such as cancer, exemplary cancers including, but not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Specifically, the present invention provides the following [1] to [21];

[1] An isolated peptide comprising an amino acid sequence of SEQ ID NO: 3.

[2] An isolated peptide, having cytotoxic T lymphocyte (CTL) inducibility, wherein the peptide comprises an amino acid sequence of SEQ ID NO: 3, wherein 1, 2, or several amino acid(s) are substituted, deleted, or added,

[3] The isolated peptide of [2], wherein the peptide has one or both of the following characteristics:

(a) second amino acid from the N-terminus is or is modified to be an amino acid selected from the group consisting of leucine and methionine; and (b) C-terminal amino acid is or is modified to be an amino acid selected from the group consisting of valine and leucine,

[4] The isolated peptide of any one of [1] to [3], wherein said peptide is nonapeptide,

[5] An isolated polynucleotide encoding the peptide of any one of [1] to [4],

[6] An agent for inducing CTL, wherein the agent comprises one or more of the peptide(s) of any one of [1] to [4], or one or more of the polynucleotide(s) of [5],

[7] A pharmaceutical agent for the treatment and/or prophylaxis of cancer, and/or the prevention of a postoperative recurrence thereof, wherein the agent comprises one or more of the peptide(s) of any one of [1] to [4], or one or more of the polynucleotides of [5],

[8] The pharmaceutical agent of [7] formulated for the administration to a subject whose HLA-A antigen is HLA-A2,

[9] The pharmaceutical agent of [8], wherein the HLA-A2 is HLA-A*0201,

[10] The pharmaceutical agent of [7] or [8], wherein the agent is formulated for the treatment of cancer,

[11] A method for inducing an antigen-presenting cell (APC) with CTL inducibility, comprising a step selected from the group consisting of:
(a) contacting an APC with the peptide of any one of [1] to [4] in vitro, ex vivo or in vivo, and
(b) introducing a polynucleotide encoding the peptide of any one of [1] to [4] into an APC,

[12] A method for inducing CTL, comprising a step selected from the group consisting of:
(a) co-culturing CD8 positive T cells with APCs that presents on its surface a complex of an HLA antigen and the peptide of any one of [1] to [4];
(b) co-culturing CD8 positive T cells with exosomes that presents on its surface a complex of an HLA antigen and a peptide as of any one of [1] to [4]; and
(c) introducing a gene that comprises a polynucleotide encoding a T cell receptor (TCR) subunit polypeptide capable of binding to the peptide of any one of [1] to [4] into a T cell,

[13] An isolated APC that presents on its surface a complex of an HLA antigen and the peptide of any one of [1] to [4],

[14] The APC of [13], which is induced by the method of [11],

[15] An isolated CTL that targets the peptide of any one of [1] to [4],

[16] The CTL of [15], which is induced by the method of [12],

[17] A method of inducing an immune response against cancer in a subject, wherein the method comprises administering to the subject an agent comprising one or more peptide(s) of any one of [1] to [4], one or more immunologically active fragment(s) thereof, or one or more polynucleotide(s) encoding the peptide(s) or the fragment(s),

[18] An antibody or fragment thereof against the peptides of any one of [1] to [4],

[19] A vector comprising a nucleotide sequence encoding the peptide of any one of [1] to [4],

[20] A host cell transformed or transfected with the vector of [19], and

[21] A diagnostic kit comprising the peptide of any one of [1] to [4], the nucleotide of [5] or the antibody of [18].

It is to be understood that both the foregoing summary of the present invention and the following detailed description are of exemplified embodiments, and not restrictive of the present invention or other alternate embodiments of the present invention.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

FIG. 2a-d is composed of a series of line graphs, (a) to (d), depicting the results of an IFN-gamma ELISA assay demonstrating the IFN-gamma production of CTL lines stimulated with TTK-A02-9-462 (SEQ ID NO: 1) (a), TTK-A02-9-630 (SEQ ID NO: 2) (b), TTK-A02-9-593 (SEQ ID NO: 3) (c), and TTK-A02-9-719 (SEQ ID NO: 6) (d). The results demonstrate that CTL lines established by stimulation with certain TTK peptides and the CTL clone established from the CTL line showed potent IFN-gamma production as compared with the control. In the figures, "+" indicates the IFN-gamma production against target cells pulsed with the appropriate peptides and "−" indicates the IFN-gamma production against target cells not pulsed with any peptides.

FIG. 2e-g is composed of a series of line graphs, (e) to (g), depicting the results of an IFN-gamma ELISA assay demonstrating the IFN-gamma production of CTL lines stimulated with TTK-A02-9-142 (SEQ ID NO: 15) (e) and TTK-A02-10-462 (SEQ ID NO: 22) (f), and the IFN-gamma production of a CTL clone established from a CTL line stimulated with TTK-A02-9-593 (SEQ ID NO: 3) by the stimulation with the same peptide (g). The results demonstrate that CTL lines established by stimulation with certain TTK peptides and the CTL clone established from the CTL line showed potent IFN-gamma production as compared with the control. In the figures, "+" indicates the IFN-gamma production against target cells pulsed with the appropriate peptides and "−" indicates the IFN-gamma production against target cells not pulsed with any peptides.

FIG. 4 is composed of a set of line graphs depicting the specific CTL inducing activity of peptides derived from TTK against target cells exogenously expressing TTK and HLA-A*0201 (Endo assay results). The graphs corresponds to FIGS. 8b, c, d and e set forth in Applicants' WO2008/102557.

DESCRIPTION OF EMBODIMENTS

Figure 1:
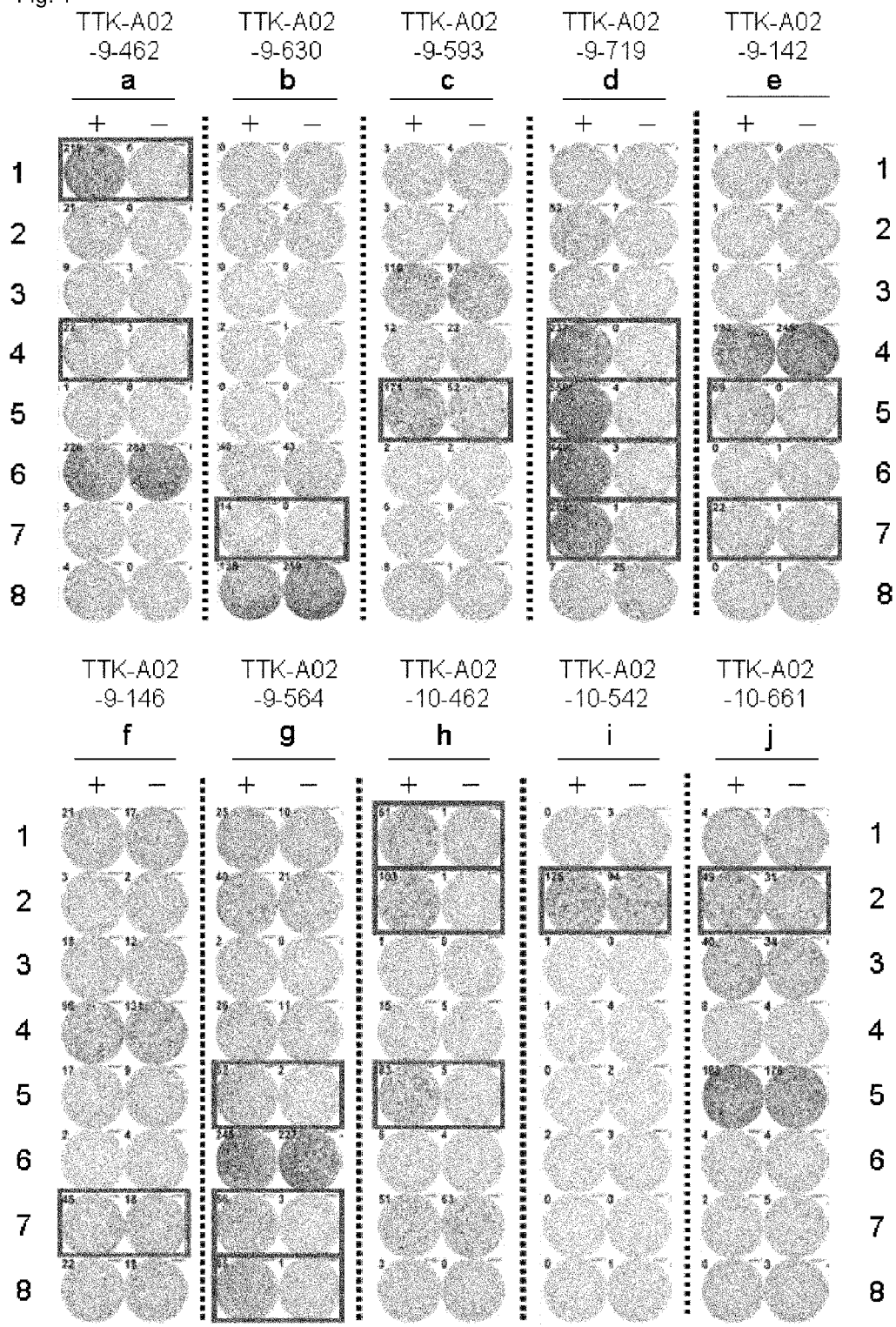
FIG. 1 is composed of a series of photographs, (a) to (j), depicting the results of IFN-gamma ELISPOT assays on CTLs that were induced with peptides derived from TTK. The CTLs in the following well numbers showed potent IFN-gamma production as compared with the control: well #1 and #4 stimulated with TTK-A02-9-462 (SEQ ID NO: 1) (a), #7 with TTK-A02-9-630 (SEQ ID NO: 2) (b), #5 with TTK-A02-9-593 (SEQ ID NO: 3) (c), #4, #5, #6 and #7 with TTK-A02-9-719 (SEQ ID NO: 6) (d), #5 and #7 with TTK-A02-9-142 (SEQ ID NO: 15) (e), #7 with TTK-A02-9-146 (SEQ ID NO: 19) (f), #5, #7 and #8 with TTK-A02-9-564 (SEQ ID NO: 20) (g), #1, #2 and #5 with TTK-A02-10-462 (SEQ ID NO: 22) (h), #2 with TTK-A02-10-542 (SEQ ID NO: 34) (i) and #2 with TTK-A02-10-661 (SEQ ID NO: 35) (j). The cells in the wells denoted with a rectangular box were expanded to establish CTL lines. In the figures, "+" indicates the IFN-gamma production against target cells pulsed with the appropriate peptide, and "−" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and/or optimization. It is also to be understood that the terminology used in the description is for the purpose of describing the particular versions or embodiments only, and is not intended to limit the scope of the present invention which will be limited only by the appended claims.

All publication, patent or patent application mentioned in this specification are specifically incorporated by reference herein in their entirety. However, nothing herein is to be construed as an admission that the invention is not entitled to antedate such disclosure by virtue of prior invention.

I. DEFINITIONS

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are, similarly to amino acids, referred to by their commonly accepted single-letter codes.

The term "composition" as used herein is intended to encompass a product including the specified ingredients in the specified amounts, as well as any product that results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the phrase "pharmaceutical composition" encompasses any composition made by admixing a compound of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the active ingredient(s) from one organ, or portion of the body, to another organ, or portion of the body.

Unless otherwise defined, the term "cancer" refers to the cancers or tumors that overexpress TTK gene, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Unless otherwise defined, the term "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A2", as used herein, representatively refers to the subtypes such as HLA-A*0201 and HLA-A*0206.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

To the extent that the methods and compositions of the present invention find utility in the context of the "treatment" of cancer, a treatment is deemed "efficacious" if it leads to clinical benefit such as, reduction in expression of TTK gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which the present invention belongs.

II. PEPTIDES

To demonstrate that peptides derived from TTK function as an antigen recognized by CTLs, peptides derived from TTK (SEQ ID NO: 40) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from TTK were identified based on their binding affinities to HLA-A2. After in vitro stimulation of T-cells by dendritic cells (DCs) pulsed (loaded) with these peptides, CTLs were successfully established using each of the following peptides:

TTK-A02-9-462 (SEQ ID NO: 1),
TTK-A02-9-630 (SEQ ID NO: 2),
TTK-A02-9-593 (SEQ ID NO: 3),
TTK-A02-9-719 (SEQ ID NO: 6),
TTK-A02-9-142 (SEQ ID NO: 15) and
TTK-A02-10-462 (SEQ ID NO: 22).

These established CTLs showed potent specific CTL activity against target cells pulsed with respective peptides. These results herein demonstrate that TTK is an antigen recognized by CTLs and that the peptides tested are epitope peptides of TTK restricted by HLA-A2.

Further, CTLs established with TTK-A02-9-593 (SEQ ID NO: 3) showed more potent specific CTL activity against target cells expressing HLA-A*0201 and TTK than reported before. These results demonstrate TTK-A02-9-593 (SEQ ID NO: 3) is a suitable peptide to induce potent specific CTL activity against cells over-expressing TTK.

Since the TTK gene is over-expressed in cancer cells and tissues, including, but not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor but not expressed in most normal organs, it represents a good target for cancer immunotherapy. Thus, the present invention provides nonapeptides (peptides consisting of nine amino acid residues) and decapeptides (peptides consisting of ten amino acid residues) corresponding to CTL-recognized epitopes from TTK. Alternatively, the present invention provides isolated peptides that bind to HLA antigens and induce cytotoxic T lymphocytes (CTLs), wherein the peptide consists of the amino acid sequence of SEQ ID NO: 40 or is an immunologically active fragment thereof. Particularly preferred examples of nonapeptides and decapeptides of the present invention include peptides having the amino acid sequence of SEQ ID NO: 3.

Generally, software programs presently available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in: Journal of Immunological Methods, 1995, 185: 181-190; and Protein Science, 2000, 9: 1838-1846. Therefore, one can select fragments derived from TTK, which have high binding affinity with HLA antigens using such software programs.

Thus, the present invention encompasses peptides composed of any fragments derived from TTK that bind with HLA antigens by such known programs. Furthermore, such peptides may include the peptide consisting of the full length of TTK.

The nonapeptides and decapeptides of the present invention may be flanked with additional amino acid residues, so long as the resulting peptides retain their CTL inducibility. The additional amino acid residues may be composed of any kind of amino acids so long as they do not impair the CTL inducibility of the original peptide. Thus, the present invention encompasses peptides with binding affinity to HLA antigens, including peptides derived from TTK. Such peptides are, for example, less than about 40 amino acids, often less than about 20 amino acids, and usually less than about 15 amino acids.

In general, the modifications of one, two or more amino acids in a peptide will not influence the function of the peptide, and in some cases will even enhance the desired function of the original protein. In fact, modified peptides (i.e., peptides composed of an amino acid sequence, in which one, two or several amino acid residues have been modified (i.e., substituted, added, deleted or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention have both CTL inducibility and an amino acid sequence of SEQ ID NO: 3, wherein one, two or even more amino acids are added, deleted and/or substituted.

Those of skill in the art will recognize that individual additions deletions or substitutions to an amino acid sequence that alter a single amino acid or a small percentage of amino acids tend to result in the conservation of the properties of the original amino acid side-chain. As such, they are often referred to as "conservative substitutions" or "conservative modifications", wherein the alteration of a protein results in modified protein having a function analogous to the original protein. Conservative substitution tables providing functionally similar amino acids are well known in the art. Examples of amino acid side chain characteristics that are desirable to conservative include, for example: hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and may include non-conservative modifications, so long as the resulting modified peptide retains the CTL inducibility of the original peptide. Furthermore, modified peptides should not exclude CTL inducible peptides of polymorphic variants, interspecies homologues, and alleles of TTK.

To retain the requisite CTL inducibility one can modify (insert, add, delete and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, and even more preferably 10% or less or 1 to 5%.

When used in the context of cancer immunotherapy, the present peptides should be presented on the surface of a cell or exosome, preferably as a complex with an HLA antigen. Therefore, it is preferable to select peptides that not only induce CTLs but also possess high binding affinity to the HLA antigen. To that end, the peptides can be modified by substitution, insertion, and/or addition of the amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, it may be desirable to substitute the second amino acid from the N-terminus with leucine or methionine, and/or the amino acid at the C-terminus with valine or leucine in order to increase the HLA-A2 binding affinity. Thus, peptides having an amino acid sequence of SEQ ID NO: 3 wherein the second amino acid from the N-terminus is substituted with leucine or methionine, and/or wherein the C-terminus is substituted with valine or leucine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, $p53_{(264-272)}$, $Her-2/neu_{(369-377)}$ or $gp100_{(209-217)}$ (Zaremba et al. Cancer Res. 57, 4570-4577, 1997, T. K. Hoffmann et al. J Immunol. (2002) Feb. 1; 168 (3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids may also be added to the N and/or C-terminus of the present peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders or allergic symptoms against specific substances may be induced. Therefore, it is preferable to perform homology searches using available databases to avoid situations in which the sequence of the peptide matches the amino acid sequence of another protein. When it becomes clear from the homology searches that there exists not even a peptide with 1 or 2 amino acids differences as compared to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic T lymphocytes (CTLs) when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8 positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC (HLA) class II restricted T(H) response) can be used. For example, the target cells may be radiolabeled with $^{51}Cr$ and such, and cytotoxic activity may be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that a nonapeptide consisting of the amino acid sequence indicated by SEQ ID NO: 3 showed particularly high CTL inducibility as well as high binding affinity to an HLA antigen. Thus, such peptide is a preferred exemplified embodiment of the present invention.

Furthermore, the result of homology analysis showed that the peptide does not have significant homology with peptides derived from any other known human gene products. Accordingly, the possibility of unknown or undesired immune responses arising when used for immunotherapy is lowered. Therefore, also from this aspect, the peptide having an amino acid sequence of SEQ ID NO: 3 find use for eliciting immunity in cancer patients against TTK. Thus, the peptides of the present invention, preferably, peptides having an amino acid sequence of SEQ ID NO: 3.

In addition to the above-described modifications, the peptides of the present invention may also be linked to other peptides, so long as the resulting linked peptide retains the requisite CTL inducibility of the original peptide. Examples of suitable other peptides include: other CTL inducible peptides derived from TTK (e.g., peptides having the amino acid sequence selected from among SEQ ID NO: 1, 2, 6, 15 and 22) or the CTL inducible peptides derived from other TAAs. Suitable inter-peptide linkers are well known in the art, for example, AAY (P. M. Daftarian et al., J Trans Med 2007, 5:26), AAA, NKRK (R. P. M. Sutmuller et al., J Immunol. 2000, 165: 7308-7315) or K (S. Ota et al., Can Res. 62, 1471-1476, K. S. Kawamura et al., J Immunol. 2002, 168: 5709-5715).

For example, non-TTK tumor associated antigen peptides also can be used substantially simultaneously to increase the immune response via HLA class I and/or class II. It is well established that cancer cells can express more than one tumor associated gene. Thus, it is within the scope of routine experimentation for one of ordinary skill in the art to determine whether a particular subject expresses additional tumor associated genes, and then to include HLA class I and/or HLA class II binding peptides derived from expression products of such genes in TTK compositions or vaccines according to the present invention.

Examples of HLA class I and HLA class II binding peptides are known to one of ordinary skill in the art (for example, see Coulie, Stem Cells 13:393-403, 1995), and can be used in the present invention in a like manner as those disclosed herein. Thus, those of ordinary skill in the art can readily prepare polypeptides including one or more TTK peptides and one or more of the non-TTK peptides, or nucleic acids encoding such polypeptides, using standard procedures of molecular biology.

The above linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J Immunol. 157(2):822-826, 1996; Tarn et al., J Exp. Med. 171(1):299-306, 1990). Polytopes containing various numbers and combinations of epitopes can be prepared and tested for recognition by CTLs and for efficacy in increasing an immune response.

The peptides of the present invention can also be linked to other substances, so long as the resulting linked peptide retain the requisite CTL inducibility of the original peptide. Examples of suitable substances include: for example, peptides, lipids, sugar and sugar chains, acetyl groups, natural and synthetic polymers, etc. The peptides may contain modifications such as glycosylation, side chain oxidation, or phosphorylation, etc., provided that the modifications do not destroy the biological activity of the original peptide. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adapted to the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted and/or added by one, two or several amino acid residues, those having same or higher activity as compared to original peptides can be screened for or selected. The present invention, therefore, also provides the method of screening for or selecting modified peptides having same or higher activity as compared to originals. An illustrative method may include the steps of:

a: substituting, deleting or adding at least one amino acid residue of a peptide of the present invention, b: determining the activity of the peptide produced in the step (a), and c: selecting the peptide having same or higher activity as compared to the original.

Herein, the activity to be assayed may include MHC binding activity, APC or CTL inducibility and cytotoxic activity. Preferably, the activity to be assayed is CTL inducibility and such activity can be assayed using the methods described in "EXAMPLES"

Herein, the peptides of the present invention may also be described as "TTK peptide(s)" or "TTK polypeptide(s)".

III. PREPARATION OF TTK PEPTIDES

The peptides of the present invention may be prepared using well known techniques. For example, the peptides may be prepared synthetically, using recombinant DNA technology or chemical synthesis. The peptides of the present invention may be synthesized individually or as longer polypeptides including two or more peptides. The peptides may then be isolated, i.e., purified or isolated so as to be substantially free from other naturally occurring host cell proteins and fragments thereof, or any other chemical substances.

The peptides of the present invention may contain modifications, such as glycosylation, side chain oxidation, or phosphorylation, provided such modifications do not destroy the biological activity of the original peptide. Other illustrative modifications include incorporation of D-amino acids or other amino acid mimetics that may be used, for example, to increase the serum half life of the peptides.

A peptide of the present invention may be obtained through chemical synthesis based on the selected amino acid sequence. Examples of conventional peptide synthesis methods that may be adapted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides may be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. POLYNUCLEOTIDES

The present invention also provides polynucleotides which encode any of the aforementioned peptides of the present invention. These include polynucleotides derived from the natural occurring TTK gene (GenBank Accession No. NM_003318 (for example, SEQ ID NO: 39)) as well as those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) may be modified to yield a functionally identical molecule. Accordingly, each silent variation of a nucleic acid that encodes a peptide is implicitly described in each disclosed sequence.

The polynucleotide of the present invention may be composed of DNA, RNA, or derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides that contain a peptide of the present invention and other epitope peptides with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J 1984, 3: 801-5.

V. EXOSOMES

The present invention further provides intracellular vesicles called exosomes, which present complexes formed between the peptides of the present invention and HLA antigens on their surface. Exosomes may be prepared, for example, using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, in a fashion similar to the peptides of the present invention.

The type of HLA antigens included in the complexes must match that of the subject requiring treatment and/or prevention. For example, in the Japanese population, HLA-A2, particularly HLA-A*0201 and HLA-A*0206, are prevalent and therefore would be appropriate for treatment of Japanese patients. The use of A24 type or the A2 type that is highly expressed among the Japanese and Caucasian is favorable for obtaining effective results, and subtypes such as A*0201 and A*0206 also find use. Typically, in the clinic, the type of HLA antigen of the patient requiring treatment is investigated in advance, which enables appropriate selection of peptides having high levels of binding affinity to the particular antigen, or having CTL inducibility by antigen presentation. Furthermore, in order to obtain peptides having both high binding affinity and CTL inducibility, substitution, insertion, deletion, and/or addition of 1, 2, or several amino acids may be performed based on the amino acid sequence of the naturally occurring TTK partial peptide.

In the present invention, peptides having a amino acid sequence of SEQ ID NO: 3 may be preferably used as peptides to be presented by exosomes, and such peptides have high binding affinity with HLA-A2 such as HLA-A*0201. Thus, in preferred embodiment, the exosomes of the present invention present complexes formed between the peptide having an amino acid sequence of SEQ ID NO: 3 and HLA antigens on their surface.

VI. ANTIGEN-PRESENTING CELLS (APCS)

The present invention also provides isolated antigen-presenting cells (APCs) that present complexes formed with HLA antigens and the peptides of the present invention on its surface. The APCs may be derived from patients who are subject to treatment and/or prevention, and may be administered as vaccines by themselves or in combination with other drugs including the peptides of the present invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing activity among APCs, DCs find use as the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:
 a: collecting APCs from a first subject,
 b: contacting with the APCs of step a, with the peptide, and
 c: administering the APCs of step b to a second subject.

The first subject and the second subject may be the same individual, or may be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells. Further, the present invention also provides the peptides of the present invention for inducing antigen-presenting cells. The APCs obtained by step b may be a vaccine for treating and/or preventing cancer, including, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

According to an aspect of the present invention, the APCs have a high level of CTL inducibility. In the term of "high level of CTL inducibility", the high level is relative to the level of that by APC contacting with no peptide or peptides which may not induce the CTL. Such APCs having a high level of CTL inducibility may be prepared by a method that includes the step of transferring a polynucleotide encoding the peptide of the present invention to APCs in vitro as well as the method mentioned above. The introduced genes may be in the form of DNAs or RNAs. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

In preferred embodiments, the APCs of the present invention may be those that present complexes formed between HLA antigens and the peptides having an amino acid sequence of SEQ ID NO: 3 on its surface. More preferably, APCs carry HLA-A2 antigen such as HLA-A*0201, and present complexes formed with such HLA-A2 antigens and the peptides of the present invention (e.g., peptides having an amino acid sequence of SEQ ID NO: 3) on its surface.

VII. CYTOTOXIC T LYMPHOCYTES (CTLS)

A CTL induced against any one of the peptides of the present invention strengthens the immune response targeting cancer cells in vivo and thus may be used as vaccines, in a fashion similar to the peptides per se. Thus, the present invention provides isolated CTLs that are specifically induced or activated by any one of the present peptides.

Such CTLs may be obtained by (1) administering the peptide(s) of the present invention to a subject or (2) contacting (stimulating) subject-derived APCs, and CD8 positive cells, or peripheral blood mononuclear leukocytes in vitro with the peptide(s) of the present invention or (3) contacting CD8 positive cells or peripheral blood mononuclear leukocytes in vitro with the APCs or exosomes presenting a complex of an HLA antigen and the peptide on its surface or (4) introducing a gene that includes a polynucleotide encoding a T cell receptor (TCR) subunit capable of binding to the peptide of the present invention. Such APCs or exosomes may be prepared by the methods described above and details of the method of (4) is described bellow in section "VIII. T cell receptor (TCR)".

The CTLs of the present invention may be derived from patients who are subject to treatment and/or prevention, and may be administered by themselves or in combination with other drugs including the peptides of the present invention or exosomes for the purpose of regulating effects. The obtained CTLs act specifically against target cells presenting the peptides of the present invention, for example, the same peptides used for induction. The target cells may be cells that endogenously express TTK, such as cancer cells, or cells that are transfected with the TTK gene; and cells that present a peptide of the present invention on the cell surface due to stimulation by the peptide may also serve as targets of activated CTL attack.

VIII. T CELL RECEPTOR (TCR)

The present invention also provides a composition including nucleic acids encoding polypeptides that are capable of forming a subunit of a T cell receptor (TCR), and methods of using the same. The TCR subunits of the present invention have the ability to form TCRs that confer specificity to T cells against tumor cells presenting TTK. By using the known methods in the art, the nucleic acids encoding alpha- and beta-chains that constitute the TCR subunits of the CTL induced with one or more peptides of the present invention may be identified (WO2007/032255 and Morgan et al., J Immunol, 171, 3288 (2003)). For example, PCR methods are preferred to analyze the nucleotide sequences encoding TCR subunits. The PCR primers for the analysis can be, for example, 5'-R primers (5'-gtctaccaggcattcgcttcat-3') as 5' side primers (SEQ ID NO: 41) and 3-TRa-C primers (5'-tcagctggaccacagccgcagcgt-3') specific to TCR alpha chain C region (SEQ ID NO: 42), 3-TRb-C1 primers (5'-tcagaaatccttttctct-tgac-3') specific to TCR beta chain C1 region (SEQ ID NO: 43) or 3-TRbeta-C2 primers (5'-ctagcctctggaatcctttctctt-3') specific to TCR beta chain C2 region (SEQ ID NO: 44) as 3' side primers, but not limited thereto. The derivative TCRs may bind target cells displaying the TTK peptide with high avidity, and optionally mediate efficient killing of target cells presenting the TTK peptide in vivo and in vitro.

The nucleic acids encoding the TCR subunits may be incorporated into suitable vectors, e.g., retroviral vectors. These vectors are well known in the art. The nucleic acids or the vectors including them usefully may be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR is presented on the surface of the T cell. A specific recognition of the above complex may be confirmed by any known methods, preferred examples of which include HLA multimer staining analysis using HLA molecules and peptides of the present invention, and ELISPOT assay. By performing the ELISPOT assay, it can be confirmed whether a T cell transduced with the nucleic acid encoding the TCR subunits recognizes a cell expressing HLA molecule and TTK, and the signal is transmitted intracellularly. It may also be confirmed whether the TCR subunits introduced into a T cell can give a T cell cytotoxic activity by known methods in the art. Preferred methods include, for example, chromium release assay using HLA-A2 positive and TTK over-expressing cells.

Also, the present invention provides CTLs which are prepared by transduction with the nucleic acids encoding the TCR subunits that bind to a complex formed between the peptide of the present invention and HLA-A2 molecule such as HLA-A*0201.

The transduced CTLs are capable of homing to cancer cells in vivo, and may be expanded by well known culturing methods in vitro (e.g., Kawakami et al., J Immunol., 142, 3452-3461 (1989)). The CTLs of the present invention may be used to form an immunogenic composition useful in treating and/or preventing cancer in a patient in need of therapy or protection (WO2006/031221).

IX. PHARMACEUTICAL AGENTS OR COMPOSITIONS

Since TTK expression is specifically elevated in cancers, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor as compared with normal tissue, the peptides of the present invention or polynucleotides encoding such peptides may be used for the treatment and/or prophylaxis of cancer, and/or for preventing the postoperative recurrence thereof. Thus, the present invention provides a pharmaceutical agent or composition for treating and/or preventing the postoperative recurrence thereof, such agent or composition including as an active ingredient one or more of the peptides, or polynucleotides of the present invention. Alternatively, the present peptides may be expressed on the surface of any of the foregoing exosomes or cells, such as APCs for the use as pharmaceutical agents or compositions. In addition, the aforementioned CTLs which target any one of the peptides of the present invention may also be used as the active ingredient of the present pharmaceutical agents or compositions.

The pharmaceutical agents and compositions of the present invention can also find use as a vaccine. In the context of the present invention, the phrase "vaccine" (also referred to as an "immunogenic composition") refers to a substance that has the function to induce anti-tumor immunity upon inoculation into animals.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient selected from among:
(a) a peptide of the present invention;
(b) a nucleic acid encoding such a peptide as disclosed herein in an expressible form;

(c) an APC or an exosome presenting a peptide of the present invention on its surface; and (d) a cytotoxic T cell of the present invention in manufacturing a pharmaceutical agent or composition for treating or preventing cancer or tumor.

Alternatively, the present invention further provides an active ingredient selected from among:

(a) a peptide of the present invention;

(b) a nucleic acid encoding such a peptide as disclosed herein in an expressible form;

(c) an APC or an exosome presenting a peptide of the present invention on its surface; and (d) a cytotoxic T cell of the present invention for use in the treatment or prevention of cancer or tumor.

Alternatively, the present invention further provides a method or process for manufacturing a pharmaceutical agent or composition for treating or preventing cancer or tumor, wherein the method or process includes the step of formulating a pharmaceutically or physiologically acceptable carrier with an active ingredient selected from among:

(a) a peptide of the present invention;

(b) a nucleic acid encoding such a peptide as disclosed herein in an expressible form;

(c) an APC or an exosome presenting a peptide of the present invention on its surface; and (d) a cytotoxic T cell of the present invention as active ingredients.

In another embodiment, the present invention also provides a method or process for manufacturing a pharmaceutical agent or composition for treating or preventing cancer or tumor, wherein the method or process includes the steps of admixing an active ingredient with a pharmaceutically or physiologically acceptable carrier, wherein the active ingredient is selected from among:

(a) a peptide of the present invention;

(b) a nucleic acid encoding such a peptide as disclosed herein in an expressible form;

(c) an APC or an exosome presenting a peptide of the present invention on its surface; and (d) a cytotoxic T cell of the present invention.

According to the present invention, peptides having an amino acid sequence of SEQ ID NOs: 3 have been found to be HLA-A2 restricted epitope peptides or the candidates that may induce potent and specific immune response. Therefore, the present pharmaceutical agents or compositions which include at least one peptide with the amino acid sequences of SEQ ID NOs: 3 are particularly suited for the administration to subjects whose HLA-A antigen is HLA-A2. The same applies to pharmaceutical agents or compositions that include polynucleotides encoding any of these peptides (i.e., the polynucleotides of the present invention).

Cancers to be treated by the pharmaceutical agents or compositions of the present invention are not limited and include any cancer in which TTK is involved (e.g., is overexpressed), including, for example, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present pharmaceutical agents or compositions may contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention may optionally include other therapeutic substances as an active ingredient, so long as the substance does not inhibit the antitumoral effect of the active ingredient, e.g., any of the present peptides. For example, formulations may include anti-inflammatory agents, pain killers, chemotherapeutics, and the like. In addition to other therapeutic substances in the medicament itself, the medicaments of the present invention may also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents or compositions of the present invention may include other agents conventional in the art having regard to the type of formulation in question.

In one embodiment of the present invention, the present pharmaceutical agents or compositions may be included in articles of manufacture and kits containing materials useful for treating the pathological conditions of the disease to be treated, e.g., cancer. The article of manufacture may include a container of any of the present pharmaceutical substances or compositions with a label. Suitable containers include bottles, vials, and test tubes. The containers may be formed from a variety of materials, such as glass or plastic. The label on the container should indicate the substance or composition is used for treating or prevention of one or more conditions of the disease. The label may also indicate directions for administration and so on.

In addition to the container described above, a kit including a pharmaceutical agent or composition of the present invention may optionally further include a second container housing a pharmaceutically-acceptable diluent. It may further include other materials desirable from a commercial and user standpoint, including other buffers, diluents, filters, needles, syringes, and package inserts with instructions for use. The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of the present invention can be administered directly as a pharmaceutical agent or composition, or if necessary, may be formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared as a combination composed of two or more of peptides of the present invention and other epitope peptides (e.g., peptides derived from other TAAs), to induce CTL in vivo. The peptide combination can take the form of a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are readministered to the subjects to induce CTLs in the subjects, and as a result, aggressiveness towards the tumor-associated endothelium can be increased.

The pharmaceutical agents or compositions for the treatment and/or prevention of cancer, including a peptide of the present invention as the active ingredient, can also include an adjuvant known to effectively establish cellular immunity. Alternatively, the pharmaceutical compositions can be administered with other active ingredients or administered by formulation into granules. An adjuvant refers to any compound, substance or composition that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like. Examples of preferred salts include salts with an alkali metal, salts with a metal, salts with an organic base, salts with an organic acid and salts with an inorganic acid.

In some embodiments, the pharmaceutical agents or compositions of the present invention may further include a component that primes CTL. Lipids have been identified as agents capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoylS-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.001 mg to 1,000 mg, for example, 0.1 mg to 10 mg, and can be administered once in a few days to few months. One skilled in the art can appropriately select a suitable dose.

(2) Pharmaceutical Agents or Compositions Containing Polynucleotides as Active Ingredient The pharmaceutical agents or compositions of the present invention can also include nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. METHODS USING THE PEPTIDES, EXOSOMES, APCS AND CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo or in vitro can include steps of:

a: collecting APCs from a subject, and
    b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides.

On the other hands, when the peptides of the present invention are administered to a subject, the APCs are contacted with the peptides in vivo, consequently, the APCs with high CTL inducibility are induced in the body of the subject. Thus, the present invention includes administering the peptides of the present invention to a subject. Similarly, when the polynucleotides of the present invention are administered to a subject in an expressible form, the peptides of the present invention are expressed and contacted with APCs in vivo, consequently, the APCs with high CTL inducibility are induced in the body of the subject. Thus, the present invention may also include administering the polynucleotides of the present invention to a subject. "Expressible form" is described above in section "IX. Pharmaceutical agents or compositions, (2) Pharmaceutical agents or compositions containing polynucleotides as the active ingredient".

The present invention may also include introducing the polynucleotide of the present invention into an APCs to induce APCs with CTL inducibility. For example, the method can include steps of:

a: collecting APCs from a subject, and
    b: introducing a polynucleotide encoding the peptide of the present invention.

Step b can be performed as described above in section "VI. Antigen-presenting cells".

Alternatively, the present invention provides a method for preparing an antigen-presenting cell (APC) which specifically induces CTL activity against TTK, wherein the method can include one of the following steps:

(a) contacting an APC with a peptide of the present invention in vitro, ex vivo or in vivo; and
    (b) introducing a polynucleotide encoding a peptide of the present invention into an APC.

(2) Method of Inducing CTLs

The present invention also provides methods for inducing CTLs using the peptides, polynucleotides, exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs may include at least one step selected from the group consisting of:

a) contacting a CD8 positive T cell with an antigen-presenting cell and/or an exosome that presents on its surface a complex of an HLA antigen and a peptide of the preset invention; and
    b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the methods of the present invention includes the step of administering the peptides, the polynucleotides, the APCs or exosomes of the present invention to a subject.

Alternatively, CTLs can be also induced by using them ex vivo or in vitro, and after inducing CTL, the activated CTLs can be returned to the subject. For example, the method can include steps of:

a: collecting APCs from a subject;
    b: contacting with the APCs of step a, with the peptide; and
    c: co-culturing the APCs of step b with CD8 positive cells.

The APCs to be co-cultured with the CD8 positive cells in above step c can also be prepared by transferring a gene that includes a polynucleotide of the present invention into APCs as described above in section "VI. Antigen-presenting cells"; though the present invention is not limited thereto, and encompasses any APC that effectively presents on its surface a complex of an HLA antigen and a peptide of the present invention.

Instead of such APCs, the exosomes that presents on its surface a complex of an HLA antigen and the peptide of the present invention can be also used. Namely, the present invention can include the step of co-culturing exosomes presenting on its surface a complex of an HLA antigen and the peptide of the present invention. Such exosomes can be prepared by the methods described above in section "V. Exosomes".

Furthermore, CTL can be induced by introducing a gene that includes a polynucleotide encoding the TCR subunit binding to the peptide of the present invention into CD8 positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods of inducing an immune response against diseases related to TTK. Suitable diseases include cancer, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The methods of the present invention may include the step of administering agent(s) or composition(s) containing any of the peptides of the present invention or polynucleotides encoding them. The inventive methods also contemplate the administration of exosomes or APCs presenting any of the peptides of the present invention. For details, see the item of "IX. Pharmaceutical agents or compositions", particularly the part describing the use of the pharmaceutical agents or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent or composition inducing immune response, wherein the method may include the step of admixing or formulating the peptide of the present invention with a pharmaceutically acceptable carrier.

Alternatively, the method of the present invention may include the step of administrating a vaccine or a pharmaceutical agent or composition that contains:

(a) a peptide of the present invention;
(b) a nucleic acid encoding such a peptide as disclosed herein in an expressible form;
(c) an APC or an exosome presenting a peptide of the present invention on its surface; or
(d) a cytotoxic T cell of the present invention.

In the context of the present invention, a cancer over-expressing TTK can be treated with these active ingredients. Examples such cancer include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Accordingly, prior to the administration of the vaccines or pharmaceutical agents or compositions including the active ingredients, it is preferable to confirm whether the expression level of TTK in the cells or tissues to be treated is enhanced compared with normal cells of the same organ. Thus, in one embodiment, the present invention provides a method for treating cancer (over)expressing TTK in a patient in need thereof, such method may include the steps of:

i) determining the expression level of TTK in cells or tissue(s) obtained from a subject with the cancer to be treated;
ii) comparing the expression level of TTK with normal control level; and
iii) administrating at least one component selected from the group consisting of (a) to (d) described above to a subject with cancer overexpressing TTK compared with normal control.

Alternatively, the present invention provides a vaccine or pharmaceutical agent or composition that includes at least one component selected from the group consisting of (a) to (d) described above, to be administered to a subject having cancer over-expressing TTK. In other words, the present invention further provides a method for identifying a subject to be treated with a TTK polypeptide of the present invention, such method including the step of determining an expression level of TTK in subject-derived cells or tissue(s), wherein an increase of the level compared to a normal control level of the gene indicates that the subject may have cancer which may be treated with the TTK polypeptide of the present invention. Methods of treating cancer of the present invention are described in more detail below.

Any subject-derived cell or tissue can be used for the determination of TTK expression so long as it includes the objective transcription or translation product of TTK. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

A subject to be treated by the present method is preferably a mammal. Exemplary mammals include, but are not limited to, e.g., human, non-human primate, mouse, rat, dog, cat, horse, and cow.

According to the present invention, the expression level of TTK in cells or tissues obtained from a subject may be determined. The expression level can be determined at the transcription (nucleic acid) product level, using methods known in the art. For example, the mRNA of TTK may be quantified using probes by hybridization methods (e.g., Northern hybridization). The detection may be carried out on a chip, an array or as such. The use of an array may be preferable for detecting the expression level of TTK. Those skilled in the art can prepare such probes utilizing the sequence information of TTK. For example, the cDNA of TTK may be used as the probes. If necessary, the probes may be labeled with a suitable label, such as dyes, fluorescent substances and isotopes, and the expression level of the gene may be detected as the intensity of the hybridized labels.

Furthermore, the transcription product of TTK (e.g., SEQ ID NO: 39) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of TTK. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

Alternatively, the translation product may be detected for the diagnosis of the present invention. For example, the quantity of TTK protein (e.g., SEQ ID NO: 40) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the TTK protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of TTK gene based on its translation product, the intensity of staining may be measured via immunohistochemical analysis using an antibody against the TTK protein. Namely, in this measurement, strong staining indicates increased presence/level of the protein and, at the same time, high expression level of TTK gene.

The expression level of a target gene, e.g., the TTK gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells by using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of TTK gene in samples from subjects whose disease states are known. Furthermore, the control level can be derived from a database of expression patterns from previously tested cells. Moreover, according to an aspect of the present invention, the expression level of TTK gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of TTK gene in a population with a known disease state. The standard value may be obtained by any method known in the art. For example, a range of mean+/−2 S.D. or mean+/−3 S.D. may be used as the standard value.

When the expression level of TTK gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:

a) determining the expression level of TTK in cells or tissue(s) obtained from a subject who is suspected to have the cancer to be treated;

b) comparing the expression level of TTK with a normal control level;

c) diagnosing the subject as having the cancer to be treated, if the expression level of TTK is increased as compared to the normal control level; and d) selecting the subject for cancer treatment, if the subject is diagnosed as having the cancer to be treated, in step c).

Alternatively, such a method may include the steps of:

a) determining the expression level of TTK in cells or tissue(s) obtained from a subject who is suspected to have the cancer to be treated;

b) comparing the expression level of TTK with a cancerous control level;

c) diagnosing the subject as having the cancer to be treated, if the expression level of TTK is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the TTK polypeptide of the present invention, which may also find use in assessing the prognosis of cancer and/or monitoring the efficacy or applicability of a cancer therapy, particularly a cancer immunotherapy. Illustrative examples of suitable cancers include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. More particularly, the kit preferably may include at least one reagent for detecting the expression of the TTK gene in a subject-derived cell, such reagent selected from the group of:

(a) a reagent for detecting mRNA of the TTK gene;

(b) a reagent for detecting the TTK protein or the immunologically fragment thereof; and (c) a reagent for detecting the biological activity of the TTK protein.

Examples of reagents suitable for detecting mRNA of the TTK gene may include nucleic acids that specifically bind to or identify the TTK mRNA, such as oligonucleotides that have a complementary sequence to a portion of the TTK mRNA. These kinds of oligonucleotides are exemplified by primers and probes that are specific to the TTK mRNA. These kinds of oligonucleotides may be prepared based on methods well known in the art. If needed, the reagent for detecting the TTK mRNA may be immobilized on a solid matrix. Moreover, more than one reagent for detecting the TTK mRNA may be included in the kit.

On the other hand, examples of reagents suitable for detecting the TTK protein or the immunologically fragment thereof may include antibodies to the TTK protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the TTK protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the TTK protein may be included in the kit.

The kit may contain more than one of the aforementioned reagents. The kit can further include a solid matrix and reagent for binding a probe against a TTK gene or antibody against a TTK peptide, a medium and container for culturing cells, positive and negative control reagents, and a secondary antibody for detecting an antibody against a TTK peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the TTK mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of TTK mRNA present in the sample. The detection sites may be configured in any suitably detectable shape and are typically in the shape of a bar or dot spanning the width of a test strip.

The kit of the present invention may further include a positive control sample or TTK standard sample. The positive control sample of the present invention may be prepared by collecting TTK positive samples and then assaying their TTK levels. Alternatively, a purified TTK protein or polynucleotide may be added to cells that do not express TTK to form the positive sample or the TTK standard sample. In the present invention, purified TTK may be a recombinant protein. The TTK level of the positive control sample is, for example, more than the cut off value.

In one embodiment, the present invention further provides a diagnostic kit including, a protein or a partial protein thereof capable of specifically recognizing the antibody of the present invention or an immunogenic fragment thereof.

Examples of partial peptides and immunogenic fragment of the proteins of the present invention contemplated herein include polypeptides composed of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. Methods for preparing a peptide or protein of the present invention are as described above.

The methods for diagnosing cancer of the present invention can be performed by determining the difference between the amount of anti-TTK antibody and that in the corresponding control sample as describe above. The subject is suspected to be suffering from cancer, if cells or tissues of the subject contain antibodies against the expression products (TTK) of the gene and the quantity of the anti-TTK antibody is determined to be more than the cut off value in level compared to that in normal control.

In another embodiment, a diagnostic kit of the present invention may include the peptide of the present invention and an HLA molecule binding thereto. A suitable method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. The complex may be used to quantify the antigen-peptide specific CTLs in the peripheral blood lymphocytes derived from the subject suspected to be suffering from cancer.

The present invention further provides methods or diagnostic reagents for evaluating the immunological response of subject using peptide epitopes as described herein. In one embodiment of the present invention, HLA restricted peptides as described herein may be used as reagents for evaluating or predicting an immune response of a subject. The immune response to be evaluated may be induced by contacting an immunogen with immunocompetent cells in vitro or in vivo. In certain embodiments, the substances or compositions employed as the reagent may be composition that may result in the production of antigen specific CTLs that recognize and bind to the peptide epitope(s). The peptide reagents need not be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the present invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer consisting of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the present invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the present invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a TTK immunogenic polypeptide. Such methods involve determining expression of a TTK HLA binding peptide, or a complex of a TTK HLA binding peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of TTK in a biological sample, such as a tumor biopsy, can also be tested by standard PCR amplification protocols using TTK primers. An example of tumor expression is presented herein and further disclosure of exemplary conditions and primers for TTK amplification can be found in WO2003/27322.

Preferred diagnostic methods involve contacting a biological sample isolated from a subject with an agent specific for the TTK HLA binding peptide to detect the presence of the TTK HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and TTK HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic methods of the present invention can be performed in either or both of in vivo and in vitro. Accordingly, biological sample can be located in vivo or in vitro in the present invention. For example, the biological sample can be a tissue in vivo and the agent specific for the TTK immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be performed using a method that allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

XI. ANTIBODIES

The present invention further provides antibodies that bind to peptides of the present invention. Preferred antibodies specifically bind to the peptide of the present invention and will not bind (or will bind weakly) to non-peptide of the present invention. Alternatively, antibodies bind to peptides of the present invention as well as the homologs thereof. Antibodies against peptides of the present invention can find use in cancer diagnostic and prognostic assays, and imaging methodologies. Similarly, such antibodies can find use in the treatment, diagnosis, and/or prognosis of other cancers, to the extent TTK is also expressed or overexpressed in cancer patient. Moreover, intracellularly expressed antibodies (e.g., single chain antibodies) may find therapeutical use in treating cancers in which the expression of TTK is involved, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention also provides various immunological assay for the detection and/or quantification of the TTK protein (SEQ ID NO: 40) or fragments thereof including polypeptides having an amino acid sequence selected from the group consisting of SEQ ID NOs: 1, 2, 3, 6, 15 and 22. Such assays may include one or more anti-TTK antibodies capable of recognizing and binding a TTK protein or fragments thereof, as appropriate. In the context of the present invention, anti-TTK antibodies binding to TTK polypeptide preferably recognize polypeptide consisting of amino acid sequences selected from the group consisting of SEQ ID NOs: 1, 2, 3, 6, 15 and 22. A binding specificity of antibody can be confirmed with inhibition test. That is, when the binding between an antibody to be analyzed and full-length of TTK polypeptide is inhibited under presence of any fragment polypeptides consisting of amino acid sequence of SEQ ID NOs: 1, 2, 3, 6, 15 and 22, it is shown that this antibody specifically binds to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the present invention may also include T cell immunogenicity assays (inhibitory or stimulatory) as well as MHC binding assays. In addition, the present invention contemplates immunological imaging methods capable of detecting cancers expressing TTK, examples of which include, but are not limited to, radioscintigraphic imaging methods using labeled antibodies of the present invention. Such assays can find clinical use in the detection, monitoring, and prognosis of TTK expressing cancers, examples of which include, but are not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention also provides antibodies that bind to the peptides of the present invention. An antibody of the present invention can be used in any form, for example, as monoclonal or polyclonal antibody, and may further include antiserum obtained by immunizing an animal such as a rabbit with the peptide of the present invention, all classes of polyclonal and monoclonal antibodies, human antibodies and humanized antibodies produced by genetic recombination.

A peptide of the present invention used as an antigen to obtain an antibody may be derived from any animal species, but is preferably derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a TTK peptide. In a preferred embodiment, an antibody of the present invention can recognize fragment peptides of TTK consisting of amino acid sequence selected from the group consisting of SEQ ID NOs: 1, 2, 3, 6, 15 and 22. Methods for synthesizing oligopeptide are well known in the arts. After the synthesis, peptides may be optionally purified prior to use as immunogen. In the context of the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the present invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the present invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the present invention. In ELISA, the antibody of the present invention is immobilized on a plate, a peptide of the present invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the present invention, by exposing an antibody of the present invention to a sample presumed to contain a peptide of the present invention, and detecting or measuring the immune complex formed by the antibody and the peptide.

Because the method of detection or measurement of the peptide according to the present invention can specifically detect or measure a peptide, the method can find use in a variety of experiments in which the peptide is used.

XII. VECTORS AND HOST CELLS

The present invention also provides a vector and host cell into which a nucleotide encoding the peptide of the present invention is introduced. A vector of the present invention may be used to keep a nucleotide, especially a DNA, of the present invention in host cell, to express a peptide of the present invention, or to administer a nucleotide of the present invention for gene therapy.

When *E. coli* is a host cell and the vector is amplified and produced in a large amount in *E. coli* (e.g., JM109, DH5 alpha, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The following examples are presented to illustrate the present invention and to assist one of ordinary skill in making and using the same. The examples are not intended in any way to otherwise limit the scope of the invention.

EXAMPLES

Materials and Methods

Cell Lines

T2 (HLA-A2), human B-lymphoblastoid cell line and COST, African green monkey kidney cell line, were purchased from ATCC. HLA-A2 positive and TTK positive tumor cell line, H1650, was purchased from ATCC. HLA-A2 negative and TTK positive cell lines, PC-3 and TE-1, were purchased from JCRB Cell bank and RIKEN Cell Bank, respectively.

Synthesis of Peptides Derived from TTK 9-mer and 10-mer peptides derived from TTK were designed based on binding affinity prediction against HLA-A*0201 molecule (SEQ ID NOs: 1 to 38). Peptides were synthesized by SIGMA (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (GM-CSF) (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were resuspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clone

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clone was expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1 \times 10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A02

The cDNA encoding an open reading frame of target genes or HLA-A*0201 was amplified by PCR. The PCR-amplified products were cloned into a vector. The plasmids were transfected into COS7, which is the target genes and HLA-A*0201-negative cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results

CTL Induction with the Predicted Peptides from TTK Restricted with HLA-A*0201

CTLs for those peptides derived from TTK were generated according to the protocols as described in "Materials and Methods". Peptide specific CTL activity was determined by IFN-gamma ELISPOT assay (FIGS. 1a-j). The following well numbers demonstrated potent IFN-gamm production as compared to the control wells: well number #1 and #4 stimulated with TTK-A02-9-462 (SEQ ID NO: 1) (a), #7 with TTK-A02-9-630 (SEQ ID NO: 2) (b), #5 with TTK-A02-9-593 (SEQ ID NO: 3) (c), #4, #5, #6 and #7 with TTK-A02-9-719 (SEQ ID NO: 6) (d), #5 and #7 with TTK-A02-9-142 (SEQ ID NO: 15) (e), #7 with TTK-A02-9-146 (SEQ ID NO: 19) (f), #5, #7 and #8 with TTK-A02-9-564 (SEQ ID NO: 20) (g), #1, #2 and #5 with TTK-A02-10-462 (SEQ ID NO: 22) (h), #2 with TTK-A02-10-542 (SEQ ID NO: 34) (i) and #2 with TTK-A02-10-661 (SEQ ID NO: 35) (j).

Establishment of CTL Line and Clone Against TTK Specific Peptides

The cells that showed peptide specific CTL activity detected by IFN-gamma ELISPOT assay in the well number #1 stimulated with TTK-A02-9-462 (SEQ ID NO: 1) (a), #7 with TTK-A02-9-630 (SEQ ID NO: 2) (b), #5 with TTK-A02-9-593 (SEQ ID NO: 3) (c), #5 with TTK-A02-9-719 (SEQ ID NO: 6) (d), #5 with TTK-A02-9-142 (SEQ ID NO: 15) (e) and #2 with TTK-A02-10-462 (SEQ ID NO: 22) (f) were expanded and CTL lines were established by limiting dilution as described in "Materials and Methods". CTL activity of those CTL lines was determined by IFN-gamma ELISA assay (FIGS. 2 a-f). All CTL lines demonstrated potent IFN-gamma production against the target cells pulsed with corresponding peptide as compared to target cells without peptide pulse.

Furthermore, the CTL clone was established by limiting dilution from the CTL lines as described in "Materials and Methods", and IFN-gamma production from the CTL clones against target cells pulsed peptide was determined by IFN-gamma ELISA assay. Potent IFN-gamma productions were determined from the CTL clone stimulated with TTK-A02-9-593 (SEQ ID NO: 3) (FIG. 2g).

Specific CTL Activity Against Target Cells Expressing TTK and HLA-A*0201

Figure 3:
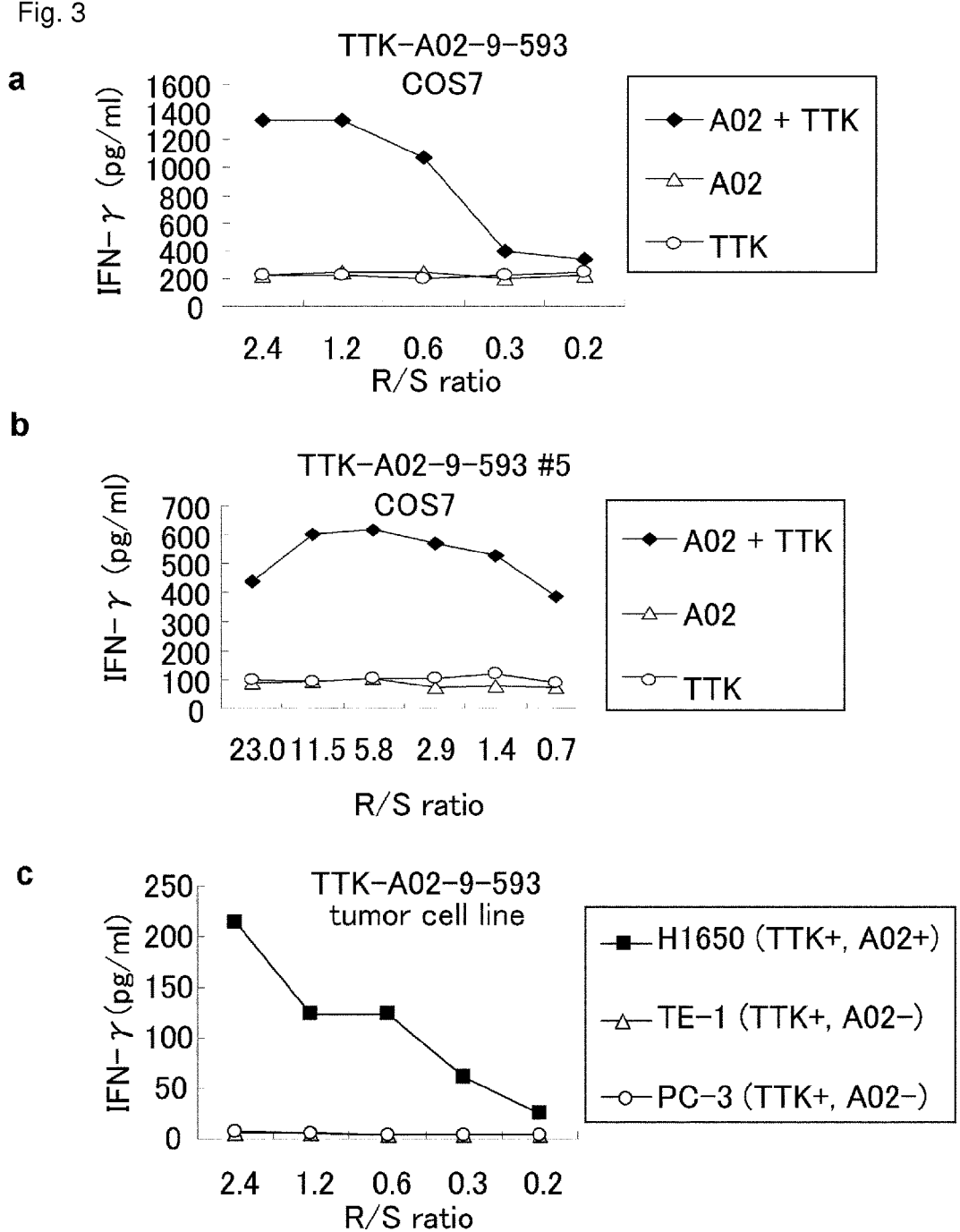
FIG. 3 is composed of a series of line graphs, (a) to (c), depicting the specific CTL activity against the target cells that exogenously express TTK and HLA-A*0201 and tumor cells that are HLA-A2 positive and overexpress TTK. COS7 cells transfected with HLA-A*0201 and the full length of TTK gene were prepared as target cells, while COS7 cells transfected with HLA-A*0201 or with the full length of TTK gene were prepared as controls, (a) and (b). Also, H1650, a tumor cell line which is HLA-A2 positive and overexpress TTK, was prepared as a target cells, while PC-3 and TE-1, tumor cell lines which are HLA-A2 negative and overexpress TTK, were prepared as controls, (c). The CTL line established with TTK-A02-9-593 (SEQ ID NO: 3) (a) and the CTL clone established from the CTL line (b) showed specific CTL activity against COS7 cells transfected with both TTK and HLA-A*0201 (black lozenge). On the other hand, no significant specific CTL activity was detected against target cells expressing either HLA-A*0201 (triangle) or TTK (circle). The CTL clone also showed specific CTL activity against tumor cell line (HLA-A2+, TTK$^+$): H1650 cells (c) (black box). On the other hand, no significant specific CTL activity was detected against target cells (HLA-A2$^-$, TTK$^+$) (triangle: PC-3, circle: TE-1).

The established CTL lines and clones raised against each peptide were examined for the ability to recognize target cells that express TTK and HLA-A*0201 molecule. Specific CTL activity against COS7 cells which transfected with both the full length of TTK and HLA-A*0201 gene (a specific model for the target cells that endogenously express TTK and HLA-A*0201 gene) was tested using the CTL lines and clones raised by corresponding peptide as the effecter cells. COS7 cells transfected with either full length of TTK genes or HLA-A*0201 were prepared as controls. In FIG. 3, the CTL line and the CTL clone stimulated with TTK-A02-9-593 (SEQ ID NO: 3) showed potent CTL activity against COS7 cells expressing both TTK and HLA-A*0201 (a: line, b:

clone). On the other hand, no significant specific CTL activity was detected against the controls. The CTL clone established with TTK-A02-9-593 (SEQ ID NO: 3) also showed specific CTL activity against a tumor cell line endogenously expressing both TTK and HLA-A*0201: H1650 cells (c). On the other hand, no significant specific CTL activity was detected against controls: TE1 cells and PC3 cells. Thus, these data clearly demonstrated that peptides of TTK-A02-9-593 (SEQ ID NO: 3) were endogenously processed and expressed on the target cells with HLA-A*0201 molecule. And then this peptide-HLA complex was recognized by the CTLs. These results indicate that TTK-A02-9-593 (SEQ ID NO: 3) may be suitable as a cancer vaccine for patients with TTK expressing tumors.

Homology Analysis of Antigen Peptides

The CTLs stimulated with TTK-A02-9-593 (SEQ ID NO: 3) showed significant and specific CTL activity. This result may be due to the fact that the sequences of TTK-A02-9-593 (SEQ ID NO: 3) are homologous to peptides derived from other molecules that are known to sensitize the human immune system. To exclude this possibility, homology analyses were performed for these peptide sequences using as queries the BLAST algorithm (available on the world wide web at ncbi.nlm.nih.gov/blast/blast.cgi) which revealed no sequence with significant homology. The results of homology analyses indicate that the sequences of TTK-A02-9-593 (SEQ ID NO: 3) are unique and thus, there is little possibility, to our best knowledge, that these molecules raise unintended immunologic response to some unrelated molecule.

In conclusion, a novel HLA-A02 epitope peptide derived from TTK was identified. Furthermore, it was demonstrated that vaccines using the epitope peptide of TTK may be applicable for cancer immunotherapy.

Reference Example

Specific CTL Activity Against the Target Cells Expressing TTK and HLA-A*0201 [WO2008/102557]

Applicants' previous application, published as WO2008/102557, discloses the specific CTL inducing activity of peptides derived from TTK against target cells exogenously expressing TTK and HLA-A*0201 (FIG. 4).

The established CTL clone raised against these peptides were examined for their ability to recognize the target cells expressing TTK and HLA-A*0201. Specific CTL activity against COS7 transfected with both the full length TTK gene and the HLA-A*0201 molecule, which is a specific model for the target cells endogenously express TTK and HLA-A*0201, was tested using as effector cells the CTL clones raised by TTK-A2-9-462 (SEQ ID NO: 1), TTK-A02-9-547 (SEQ ID NO: 5), TTK-A2-9-719 (SEQ ID NO: 6) and TTK-A2-10-462 (SEQ ID NO: 22). COS7 transfected with full length of TTK but not full length of HLA-A*0201, COS7 transfected with HLA-A*0201 but not full length of TTK (or replaced by full length of HIG2 gene) and COS7 transfected with HLA-A*0201 and pulsed with different target epitope peptides, were prepared as controls. The results demonstrate that the CTL clones raised against those peptides have the specific CTL activity against COS7 transfected with both TTK and HLA-A*0201 (FIG. 4, corresponding to FIGS. 8b, c, d and e in WO2008/102557, incorporated herein by reference in its entirety).

As compared to those peptides, TTK-A02-9-593 (SEQ ID NO: 3) identified in the present invention possesses a distinctly effective activity that increases by one or two orders of magnitude in the IFN-gamma production (FIG. 3). Therefore, the peptide of the present invention appears to be a promising target of the treatment, prophylaxis, and/or prevention of cancer, including, but not limited to, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

INDUSTRIAL APPLICABILITY

The present invention provides new TAAs, particularly those derived from TTK that may induce potent and specific anti-tumor immune responses and have applicability to a wide variety of cancer types. Such TAAs can find utility as peptide vaccines against diseases associated with TTK, e.g., cancer, more particularly, lung cancer, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide, having cytotoxic T lymphocyte (CTL) inducibility, wherein the peptide consists of an amino acid sequence of SEQ ID NO: 3, or consists of an amino acid sequence of SEQ ID NO: 3 in which 1 or 2 amino acid(s) are substituted or added.

2. The isolated peptide of claim 1, wherein the peptide has one or both of the following characteristics:
   (a) a second amino acid from the N-terminus of the amino acid sequence of SEQ ID NO: 3 is modified to be an amino acid selected from the group consisting of leucine and methionine; and
   (b) a C-terminal amino acid of the amino acid sequence of SEQ ID NO: 3 is modified to be an amino acid selected from the group consisting of valine and leucine.

3. The isolated peptide of claim 1, wherein said peptide is nonapeptide.

4. An agent for inducing CTL, wherein the agent comprises one or more of the peptide(s) of claim 1.

5. A pharmaceutical agent for the treatment of cancer, wherein the agent comprises one or more of the peptide(s) of claim 1.

6. The pharmaceutical agent of claim 5, wherein the agent is formulated for the administration to a subject whose HLA-A antigen is HLA-A2.

7. The pharmaceutical agent of claim 6, wherein the HLA-A2 is HLA-A*0201.

8. The pharmaceutical agent of claim 5, wherein the agent is formulated for the treatment of cancer.

9. A method for inducing an antigen-presenting cell (APC) with CTL inducibility comprising:
   contacting an APC with the peptide of claim 1 in vitro, ex vivo or in vivo.

10. A diagnostic kit comprising the peptide of claim 1.

11. The pharmaceutical agent of claim 6, wherein the agent is formulated for the treatment of cancer.

12. A method for inducing a CTL, comprising a step selected from the group consisting of:
   (a) co-culturing CD8 positive T cells with APCs that presents on its surface a complex of an HLA antigen and the peptide of claim 1; and
   (b) co-culturing CD8 positive T cells with exosomes that presents on its surface a complex of an HLA antigen and the peptide of claim 1.

13. A method of inducing an immune response against cancer in a subject in need thereof, wherein the method comprises administering to the subject an agent comprising one or more peptide(s) of claim 1.

* * * * *